US006988041B2

(12) United States Patent
Benson et al.

(10) Patent No.: US 6,988,041 B2
(45) Date of Patent: Jan. 17, 2006

(54) **CRYSTALLIZATION AND STRUCTURE DETERMINATION OF *STAPHYLOCOCCUS AUREUS* NAD SYNTHETASE**

(75) Inventors: Timothy E. Benson, Kalamazoo, MI (US); Donald Bryan Prince, Parchment, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 631 days.

(21) Appl. No.: 09/772,598

(22) Filed: Jan. 30, 2001

(65) Prior Publication Data

US 2003/0166233 A1 Sep. 4, 2003

Related U.S. Application Data

(60) Provisional application No. 60/179,261, filed on Jan. 31, 2000.

(51) Int. Cl.
*G06F 17/00* (2006.01)
*C12Q 1/00* (2006.01)

(52) U.S. Cl. ............................................. 702/27; 435/4
(58) Field of Classification Search ................... 435/4; 702/27
See application file for complete search history.

(56) References Cited

U.S. PATENT DOCUMENTS

2003/0054436 A1 * 3/2003 Kunsch et al. ............. 435/69.1

FOREIGN PATENT DOCUMENTS

| EP | 0786 519 A2 | 7/1997 |
|---|---|---|
| WO | WO 93/02209 A1 | 2/1993 |
| WO | WO 97/15588 A1 | 5/1997 |
| WO | WO 98/58961 A1 | 12/1998 |
| WO | WO 99/36422 A1 | 7/1999 |
| WO | WO 99/47639 A2 | 9/1999 |
| WO | WO 99/47662 A1 | 9/1999 |
| WO | WO 00/12678 A3 | 3/2000 |
| WO | WO 00/12678 A2 | 3/2000 |
| WO | WO 01/16292 A2 | 3/2001 |

OTHER PUBLICATIONS

Sambrook, J. et al. Molecular Cloning: A Laboratory Manual. Second Edition. 1989, Cold Spring Harbor Laboratory Press, pp. 17.29–17.30.*
Worthington, V. Worthington Enzyme Manual: enzymes and related biochemicals. 1993, Worthington Biochemical Corporation, section XIV.*
Crystal Screen, 2000–2002, pp. 1–2, Hampton Research, 27632 El Lazo Road, Suite 100, Laguna Niguel, California, 92677–3913.*
Drenth, Jan. Principles of Protein X–ray Crystallography. 1994. Springer–Verlag. pp. 1–18.*
Crystal from On–line Medical Dictionary [retrieved on Jan. 6, 2004]. Retrieved from the Internet: <URL:http://cancer-web.ncl.ac.uk/cgi–bin/omd?query=crystal>; 1 pg.
Frozen from On–line Medical Dictionary [retrieved on Jan. 6, 2004]. Retrieved from the Internet: <URL:http://cancer-web.ncl.ac.uk/cgi–bin/omd?query=frozen>; 1 pg.
Ice from On–line Medical Dictionary [retrieved on Jan. 6, 2004]. Retrieved from the Internet: <URL:http://cancer-web.ncl.ac.uk/cgi–bin/omd?query=ice>; 1 pg.
Stout et al., "X–Ray Structure Determination," *A Practical Guide*, Macmillan Publishing Co., Inc., New York, 1968, pp. 54–55.
Bartlett et al., "CAVEAT: A program to facilitate the structure–derived design of biologically active molecules," *Molecular Recognition: Chemical and Biological Problems*, Royal Society of Chemistry, Special Pub No. 78:182–196 (1989).
Benson et al. "An enzyme–substrate complex involved in bacterial cell wall biosynthesis," *Nat Struct Biol.* Aug. 1995;2(8):644–53.
Blundell et al., *Protein Crystallography*, Academic Press, New York, NY; title page, publication page, and table of contents only, 8 pages (1976).
Böhm, "The computer program LUDI: a new method for the de novo design of enzyme inhibitors," *J. Comput. Aided Mol. Des.* Feb. 1992;6(1):61–78.
Brünger, *X–plor Manual (Version 3.1) A System for X–ray Crystallography and NMR* (title page, publisher's page, and table of contents only), Yale University Press, New Haven, CT, 1992; 13 pgs.
Collaborative Computational Project, No. 4, "The *CCP4* suite: programs for protein crystallography" *Acta Cryst.* 1994;D50:760–3.
Cowtan et al., "Improvement of Macromolecular Electron–Density Maps by the Simultaneous Application of Real and Reciprocal Space Constraints," *Acta Crystallogr D Biol Crystallogr.* Jan. 1, 1993;49(Pt 1):148–157.
Cowtan et al., "Miscellaneous algorithms for density modification," *Acta Crystallogr D Biol Crystallogr.* Jul. 1, 1998;54(Pt 4):487–93.
Eisen et al., "HOOK: a program for finding novel molecular architectures that satisfy the chemical and steric requirements of a macromolecule binding site," *Proteins: Struct. Funct. Genet.* Jul. 1994;19(3):199–221.
Evans, "SETOR: hardware–lighted three–dimensional solid model representations of macromolecules," *J Mol Graph.* Jun. 1993;11(2):134–8, 127–8.

(Continued)

Primary Examiner—Ardin H. Marschel
Assistant Examiner—Channing S. Mahatan
(74) Attorney, Agent, or Firm—Rosanne Goodman

(57) ABSTRACT

An unliganded form of *Staphylococcus aureus* NAD synthetase (*S. aureus* NadE) has been crystallized, and the three-dimensional x-ray crystal structure has been solved to 2.3 Å resolution. The x-ray crystal structure is useful for solving the structure of other molecules or molecular complexes, and designing inhibitors of *S. aureus* NadE activity.

16 Claims, 11 Drawing Sheets

OTHER PUBLICATIONS

Finzel, "LORE: exploiting database of known structures," *Meth. Enzymol.* 1997; 277(B):230–42.

Gillet et al., "SPROUT: a program for structure generation," *J. Comput. Aided Mol. Des.* Apr. 1993;7(2):127–53.

Goodford, "A computational procedure for determining energetically favorable binding sites on biologically important macromolecules," *J Med Chem.* Jul. 1985; 28(7):849–57.

Goodsell et al., "Automated docking of substrates to proteins by simulated annealing," *Proteins: Struct. Funct. Genet.* 1990;8(3):195–202.

Hendrickson, "Determination of macromolecular structures from anomalous diffraction of synchrotron radiation," *Science.* Oct. 4, 1991;254(5028):51–8.

Hughes et al., "Structural gene for NAD synthetase in *Salmonella typhimurium*," *J Bacteriol.* May 1988;170(5):2113–20.

Jiang et al., "Protein hydration observed by X–ray diffraction. Solvation properties of penicillopepsin and neuraminidase crystal structures," *J. Mol. Biol.* Oct. 14, 1994;243(1):100–15.

Kraulis, "MOLSCRIPT: a program to produce both detailed and schematic plots of protein structures," *J. Appl. Cryst.* Oct. 1991;24:946–950.

Kuntz et al., "A geometric approach to macromolecule–ligand interactions," *J. Mol. Biol.* Oct. 25, 1982;161(2):269–88.

Laemmli, "Cleavage of Structural Proteins during the Assembly of the Head of Bacteriophage T4," *Nature*, Aug. 15, 1970;227(259):680–85.

Laskowski, et al., "PROCHECK: a program to check the stereochemical quality of protein structures," *J. Appl Cryst.* Apr. 1993;26:283–291.

Lattman, "Use of the rotation and translation functions," *Methods Enzymol.* 1985;115:55–77.

Lauri et al., "CAVEAT: a program to facilitate the design of organic molecules," *J Comput Aided Mol Des.* Feb. 1994;8(1):51–66.

Martin, "3D database searching in drug design," *J. Med. Chem.* Jun. 12, 1992; 35(12):2145–54.

Meng et al., "Automated docking with grid–based energy evaluation," *J. Comp. Chem,* May 1992;13(4):505–524.

Merritt et al., "Raster3D Version 2.0. A Program for Photorealistic Molecular Graphics", *Acta Crystallogr D Biol Crystallogr.,* 1994;50:869–73.

Miranker et al., "Functionality maps of binding sites: a multiple copy simultaneous search method," *Proteins: Struct. Funct. Genet.* 1991;11(1):29–34.

Moat et al., "Biosynthesis and salvage pathways of pyridine nucleotides. Coenzymes and cofactors, Pyridine Nucleotide Coenzymes," Eds. D. Dolphin et al. John Wiley & Sons, Inc., New York, 1987; vol. II, part B:1–24.

National Institutes of Health, "BLAST 2 Sequences," [online] United States; retrieved Oct. 15, 2001 from the Internet: <URL:http://www.ncbi.nlm.nih.gov/gorf/bl2.html>,1 pg.

Navaza, "AMoRe: an automated package for molecular replacement," *Acta Crystallogr A.* Mar. 1994;50:157–163.

Nessi et al., "The outB gene of *Bacillus subtilis* codes for NAD synthetase," *J Biol Chem.* Mar. 17, 1995;270(11):6181–5.

Nishibata et al., "Automatic creation of drug candidate structures based on receptor structure. Starting point for artificial lead generation," *Tetrahedron,* 1991;47(43):8985–90.

Otwinowski, "Maximum likelihood refinement of heavy atom parameters," *Isomorphous replacement and anomalous scattering—Proceedings of the CCP4 Study Weekend Jan. 25–26, 1991,* (W. Wolf et al., Eds.) Science and Engineering Research Counsel, Daresbury Laboratory, Warrington, U.K. (1991) pp. 80–86.

Ozment et al., "Structural study of *Escherichia coli* NAD synthetase: overexpression, purification, crystallization, and preliminary crystallographic analysis," *J. Struct. Biol.* Oct. 1999;127(3):279–82.

Ramakrishnan et al., "Crystal structure of globular domain of histone H5 and its implications for nucleosome binding," *Nature.* Mar. 18, 1993;362(6417):219–23.

Research Collaboratory for Structural Bioinformatics, "Protein Data Bank," [online] United States; retrieved Oct. 15, 2001 from the Internet: <URL:http://www.rcsb.org/pdb/> 1 page.

Rizzi et al., "Crystal structure of NH3–dependent NAD+ synthetase from *Bacillus subtilis*," *EMBO J.* Oct. 1, 1996;15(19):5125–34.

Rizzi et al., "Crystallization of NAD+ synthetase from *Bacillus subtilis,*" *Proteins.* Oct. 1996;26(2):236–8.

Rizzi et al., "A novel deamido–NAD+–binding site revealed by the trapped NAD–adenylate intermediate in the NAD+ synthetase structure," *Structure.* Sep. 15, 1998;6(9):1129–40.

Rossmann et al., "Chemical and biological evolution of nucleotide–binding protein," *Nature.* Jul. 19, 1974;250(463):194–9.

Rossmann, ed., *The Molecular Replacement Method—A Collection of Papers on the Use of Non–Crystallographic Symmetry, Intl. Sci. Rev. Ser. No. 13,* Gordon & Breach, New York, NY; title page, publication page, and table of contents only, 6 pages (1972).

Sack, "CHAIN—A Crystallographic Modeling Program," *J. Molecular Graphics.* Dec. 1988; 6(4):224–5.

Sheldrick et al., "Structure solution by iterative peaklist optimization and tangent expansion in space group P1," *Acta Crystallogr B.* Aug. 1, 1995;51(Pt 4):423–31.

Tatusova et al., "BLAST 2 Sequences, a new tool for comparing protein and nucleotide sequences," *FEMS Microbiol Lett.* May 15, 1999;174(2):247–50.

Travis, "Proteins and organic solvents make an eye–opening mix," *Science.* Nov. 26, 1993;262(5138):1374.

Van Duyne et al., "Atomic structures of the human immunophilin FKBP–12 complexes with FK506 and rapamycin," *J Mol Biol.* Jan. 5, 1993;229(1):105–24.

White et al., "Biosynthesis of salvage pathways of pyridine nucleotide coenzymes." Academic Press, New York; title page, publication page, and table of contents only, 13 pages (1982).

Willison, "An essential gene (efg) located at 38.1 minutes on the *Escherichia coli* chromosome," *J Bacteriol.* Sep. 1992;174(17):5765–6.

Willison et al., "The *Escherichia coli* efg gene and the *Rhodobacter capsulatus* adgA gene code for NH3–dependent NAD synthetase," *J Bacteriol.* Jun. 1994;176(11):3400–2.

Wyckoff et al., eds., *Methods in Enzymology vol. 114—Diffraction Methods for Biological Macromolecules*, Academic Press, Orlando, FL; title page, publication page, and table of contents only, 5 pages (1985).

Wyckoff et al., eds., *Methods in Enzymology vol. 115. Diffraction Methods for Biological Macromolecules,* Academic Press, Orlando, FL; title page, publication page, and table of contents only, 4 pages (1985).

Zalkin, "NAD synthetase," *Methods Enzymol.* 1985;113:297–302.

* cited by examiner

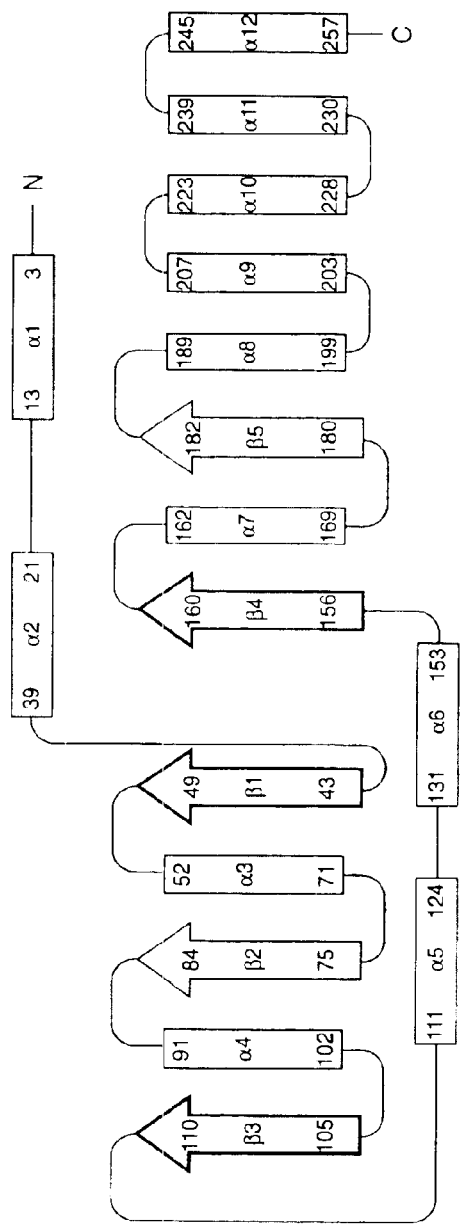
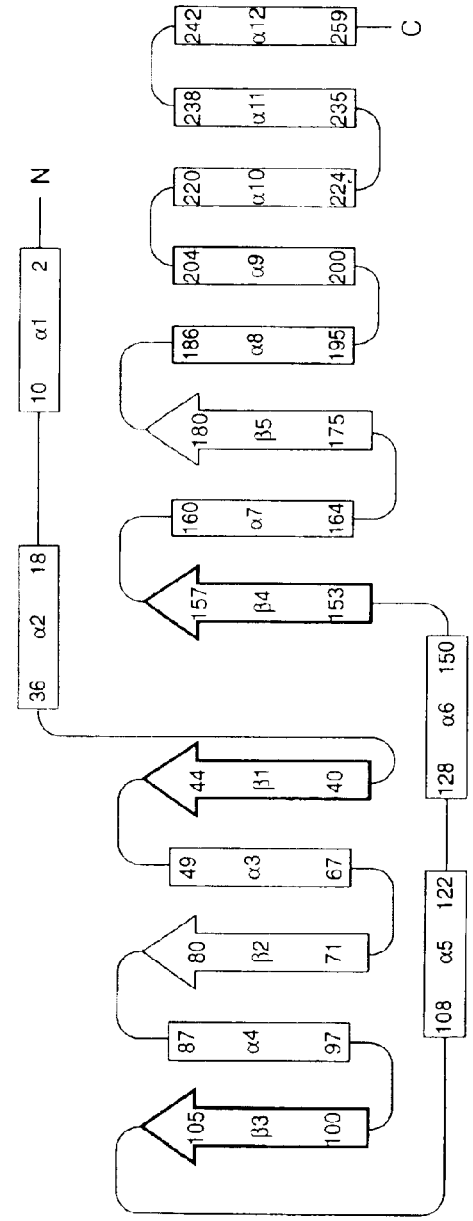
Fig. 7b
Fig. 7c

```
SEQ ID NO:2  nade_bs    (1)    1                                                              50
SEQ ID NO:1  nade_sa    (1)    ---SMQEKIMREHVKPSIDPKQEIEDRVNFLKQYVK-KTGAKGFVLGIS
                               MGSKTQEVIVQEMKVKKRIDSAEEIMELKQFIKNYVQSHSFIKSLVLGIS nade_bs    (47)   51                                                             100
             nade_sa    (51)   GGQDSTLAGRLAQLAVESIREEGGDAQFIAVRLPHGTQQDEDDAQLALKF
                               GGQDSTLVGKLVQMSVNELREEGIDCTFIAVKLPYGVQKDADEVEQALRF nade_bs    (97)   101                                                            150
             nade_sa    (101)  IKPDKSWKFDIKSTVSAFSDQYQQETGDQLTDFNKGNVKARTRMIAQYAI
                               IEPDEIVTVNIKPAVDQS-VQSLKEAGIVLTDFQKGNEKARERMKVQFSI nade_bs    (147)  151                                                            200
             nade_sa    (150)  GGQEGLEVIGTDHAAEAVTGFETKYGDGADLPLTGLTKRQGRTLLKEL
                               ASNRQGIVVGTDHSAENITGFVTKYGDGAADIAPIFGLNKRQGRQLLAYL nade_bs    (197)  201                                                            250
             nade_sa    (200)  GAPERLYLKEPTADLLDEKPQQSDETELGISYDEIDDYLEGKEVSAKVSE
                               GAPKELYEKTPTADLEDDKPQLPDEDALGVIYEAIDNYLEGKPVTPEEQK nade_bs    (247)  251                          284
             nade_sa    (250)  ALEKRYSMTEHKRQVPASMEDDWK-------
                               VIENHYIRNAHKRELAYTRYT-WPKSRSHHHHHH
```

*Fig. 9*

SEQUENCE LISTING

```
<160> NUMBER OF SEQ ID NOS:  2

<210> SEQ ID NO 1
<211> LENGTH: 282
<212> TYPE: PRT
<213> ORGANISM: S.aureus

<400> SEQUENCE: 1

Met Gly Ser Lys Leu Gln Asp Val Ile Val Gln Glu Met Lys Val Lys
 1               5                  10                  15

Lys Arg Ile Asp Ser Ala Glu Glu Ile Met Glu Leu Lys Gln Phe Ile
            20                  25                  30

Lys Asn Tyr Val Gln Ser His Ser Phe Ile Lys Ser Leu Val Leu Gly
        35                  40                  45

Ile Ser Gly Gly Gln Asp Ser Thr Leu Val Gly Lys Leu Val Gln Met
    50                  55                  60
```

```
Ser Val Asn Glu Leu Arg Glu Gly Ile Asp Cys Thr Phe Ile Ala
 65                  70                  75                  80

Val Lys Leu Pro Tyr Gly Val Gln Lys Asp Ala Asp Glu Val Glu Gln
                 85                  90                  95

Ala Leu Arg Phe Ile Glu Pro Asp Glu Ile Val Thr Val Asn Ile Lys
            100                 105                 110

Pro Ala Val Asp Gln Ser Val Gln Ser Leu Lys Glu Ala Gly Ile Val
        115                 120                 125

Leu Thr Asp Phe Gln Lys Gly Asn Glu Lys Ala Arg Glu Met Lys
    130                 135                 140

Val Gln Phe Ser Ile Ala Ser Asn Arg Gln Gly Ile Val Val Gly Thr
145                 150                 155                 160

Asp His Ser Ala Glu Asn Ile Thr Gly Phe Tyr Thr Lys Tyr Gly Asp
                165                 170                 175

Gly Ala Ala Asp Ile Ala Pro Ile Phe Gly Leu Asn Lys Arg Gln Gly
            180                 185                 190

Arg Gln Leu Leu Ala Tyr Leu Gly Ala Pro Lys Glu Leu Tyr Glu Lys
        195                 200                 205

Thr Pro Thr Ala Asp Leu Glu Asp Lys Pro Gln Leu Pro Asp Glu
    210                 215                 220

Asp Ala Leu Gly Val Thr Tyr Glu Ala Ile Asp Asn Tyr Leu Glu Gly
225                 230                 235                 240

Lys Pro Val Thr Pro Glu Gln Lys Val Ile Glu Asn His Tyr Ile
                245                 250                 255

Arg Asn Ala His Lys Arg Glu Leu Ala Tyr Thr Arg Tyr Thr Trp Pro
                260                 265                 270

Lys Ser Arg Ser His His His His His His
        275                 280

<210> SEQ ID NO 2
<211> LENGTH: 271
<212> TYPE: PRT
<213> ORGANISM: B.subtilis

<400> SEQUENCE: 2

Ser Met Gln Glu Lys Ile Met Arg Glu Leu His Val Lys Pro Ser Ile
  1               5                  10                  15

Asp Pro Lys Gln Glu Ile Glu Asp Arg Val Asn Phe Leu Lys Gln Tyr
             20                  25                  30

Val Lys Lys Thr Gly Ala Lys Gly Phe Val Leu Gly Ile Ser Gly Gly
         35                  40                  45

Gln Asp Ser Thr Leu Ala Gly Arg Leu Ala Gln Leu Ala Val Glu Ser
     50                  55                  60

Ile Arg Glu Glu Gly Gly Asp Ala Gln Phe Ile Ala Val Arg Leu Pro
 65                  70                  75                  80

His Gly Thr Gln Gln Asp Glu Asp Asp Ala Gln Leu Ala Leu Lys Phe
                 85                  90                  95

Ile Lys Pro Asp Lys Ser Trp Lys Phe Asp Ile Lys Ser Thr Val Ser
            100                 105                 110

Ala Phe Ser Asp Gln Tyr Gln Gln Glu Thr Gly Asp Gln Leu Thr Asp
        115                 120                 125

Phe Asn Lys Gly Asn Val Lys Ala Arg Thr Arg Met Ile Ala Gln Tyr
    130                 135                 140

Ala Ile Gly Gly Gln Glu Gly Leu Leu Val Leu Gly Thr Asp His Ala
145                 150                 155                 160
```

```
Ala Glu Ala Val Thr Gly Phe Phe Thr Lys Tyr Gly Asp Gly Gly Ala
                165                 170                 175

Asp Leu Leu Pro Leu Thr Gly Leu Thr Lys Arg Gln Gly Arg Thr Leu
            180                 185                 190

Leu Lys Glu Leu Gly Ala Pro Glu Arg Leu Tyr Leu Lys Glu Pro Thr
        195                 200                 205

Ala Asp Leu Leu Asp Glu Lys Pro Gln Gln Ser Asp Glu Thr Glu Leu
        210                 215                 220

Gly Ile Ser Tyr Asp Glu Ile Asp Asp Tyr Leu Glu Gly Lys Glu Val
225                 230                 235                 240

Ser Ala Lys Val Ser Glu Ala Leu Glu Lys Arg Tyr Ser Met Thr Glu
                245                 250                 255

His Lys Arg Gln Val Pro Ala Ser Met Phe Asp Asp Trp Trp Lys
                260                 265                 270
```

CRYSTALLIZATION AND STRUCTURE DETERMINATION OF *STAPHYLOCOCCUS AUREUS* NAD SYNTHETASE

This application claims the benefit of U.S. Provisional Application Ser. No. 60/179,261, filed Jan. 31, 2000, which is incorporated herein by reference in its entirety.

This application incorporates by reference the material contained on the duplicate (2) compact discs submitted herewith. Each disc contains the following files:

| Name | Size | Date of File Creation |
| --- | --- | --- |
| table__1.txt | 640 KB | Jan. 23, 2001 |
| table__2.txt | 2,903 KB | Jan. 23, 2001 |

FIELD OF THE INVENTION

This invention relates to the crystallization and structure determination of NAD synthetase (NadE) from *Staphylococcus aureus*.

BACKGROUND OF THE INVENTION

Biochemical reactions require not only the presence of enzymes in the intracellular milieu but also essential small molecule cofactors (e.g., flavins and nicotinamides). Nicotinamide adenine dinucleotide ($NAD^+$) is a common coenzyme that can serve as a conduit for electrons in oxidation/reduction reactions as well as a source of ADP in protein ADP-ribosylation. The synthesis of $NAD^+$ can occur either through de novo synthesis or by a pyridine nucleotide salvage pathway. The de novo synthesis involves the conversion of L-aspartic acid into nicotinic acid mononucleotide (NAM) which is subsequently converted to nicotinic acid adenine dinucleotide, also known as deamino-$NAD^+$ ($N^aAD$). NAD synthetase (NadE) catalyzes the final reaction in the biosysthesis of $NAD^+$. The substrate deamino-$NAD^+$ combines with ATP to form the bound intermediate, NAD-adenylate. Ammonia is then added to the nicotinic acid carboxylate, releasing $NAD^+$ and AMP (FIG. 1).

NAD synthetase belongs to a family of enzymes known as N-type ATP pyrophosphatases which share a common mechanism for adenylation of their substrates prior to amidation reactions. NAD synthetase also belongs to a class of enzymes known as amidotransferases which transfer ammonia to their substrates. Amidotransferases are typically characterized by the presence of two domains (present in a single polypeptide or as independent polypeptide subunits) one of which generates ammonia utilizing glutamine as a nitrogen source (glutamine amide transfer (GAT) domain), and the other which is responsible for the actual transfer of ammonia to the substrate. However the *S. aureus* NAD synthetase, like the *Bacillus subtilis* enzyme, does not contain a GAT domain and instead takes advantage of free ammonia as its nitrogen source. A separate GAT protein has yet to be identified in these organisms.

The gene encoding for the NAD synthetase has been shown to be essential for cell growth in several species including *Bacillus subtilis, Escherichia coli, Salmonella typhimurium*, and *Rhodobacter capsulatus*. Thus, identification of compounds that specifically inhibit the activity of bacterial NAD synthetase would have great therapeutic significance.

SUMMARY OF THE INVENTION

In one aspect, the present invention provides a molecule or molecular complex including at least a portion of an *S. aureus* NAD synthetase or NAD synthetase-like substrate binding pocket, wherein the substrate binding pocket includes the amino acids listed in Table 3, the substrate binding pocket being defined by a set of points having a root mean square deviation of less than about 1.1 Å from points representing the backbone atoms of the amino acids as represented by the structure coordinates listed in Table 1. Preferably the substrate binding pocket includes the amino acids listed in Table 4. More preferably the substrate binding pocket includes the amino acids listed in Table 5.

In another aspect, the present invention provides a molecule or molecular complex that is structurally homologous to an *S. aureus* NAD synthetase molecule or molecular complex, wherein the *S. aureus* NAD synthetase molecule or molecular complex is represented by at least a portion of the structure coordinates listed in Table 1.

In another aspect, the present invention provides a scalable three-dimensional configuration of points. In one embodiment, at least a portion of the points are derived from structure coordinates of at least a portion of an *S. aureus* NAD synthetase molecule or molecular complex listed in Table 1 including at least one of an *S. aureus* NAD synthetase or NAD synthetase-like substrate binding pocket. Preferably, substantially all of the points are derived from structure coordinates of an *S. aureus* NAD synthetase molecule or molecular complex listed in Table 1. Preferably at least a portion of the points derived from the *S. aureus* NAD synthetase structure coordinates are derived from structure coordinates representing the locations of at least the backbone atoms of amino acids defining an *S. aureus* NAD synthetase substrate binding pocket, the substrate binding pocket including the amino acids listed in Table 3. More preferably, the substrate binding pocket includes the amino acids listed in Table 4. Most preferably, the substrate binding pocket includes the amino acids listed in Table 5. Advantageously, the scalable three-dimensional configuration of points may be displayed as a holographic image, a stereodiagram, a model or a computer-displayed image.

In another embodiment, at least a portion of the points of the scalable three-dimensional configuration of points are derived from structure coordinates of at least a portion of a molecule or a molecular complex that is structurally homologous to an *S. aureus* NAD synthetase molecule or molecular complex and includes at least one of an *S. aureus* NAD synthetase or NAD synthetase-like substrate binding pocket. Advantageously the scalable three-dimensional configuration of points may be displayed as a holographic image, a stereodiagram, a model or a computer-displayed image.

In another aspect, the present invention provides a machine-readable data storage medium including a data storage material encoded with machine readable data which, when using a machine programmed with instructions for using the data, is capable of displaying a graphical three-dimensional representation of at least one molecule or molecular complex selected from the group consisting of: (i) a molecule or molecular complex including at least a portion of an *S. aureus* NAD synthetase or NAD synthetase-like substrate binding pocket including the amino acids listed in Table 3, the substrate binding pocket being defined by a set of points having a root mean square deviation of less than about 1.1 Å from points representing the backbone atoms of the amino acids as represented by structure coordinates listed in Table 1; and (ii) a molecule or molecular complex that is structurally homologous to an *S. aureus* NAD synthetase molecule or molecular complex, wherein the *S. aureus* NAD synthetase molecule or molecular complex is represented by at least a portion of the structure coordinates listed in Table 1.

In another aspect, the present invention provides a machine-readable data storage medium including a data storage material encoded with a first set of machine readable data which, when combined with a second set of machine readable data, using a machine programmed with instructions for using the first set of data and the second set of data, can determine at least a portion of the structure coordinates corresponding to the second set of machine readable data, wherein the first set of data includes a Fourier transform of at least a portion of the structure coordinates for *S. aureus* NAD synthetase listed in Table 1; and the second set of data includes an x-ray diffraction pattern of a molecule or molecular complex of unknown structure.

In another aspect, the present invention provides a method for obtaining structural information about a molecule or a molecular complex of unknown structure including: crystallizing the molecule or molecular complex; generating an x-ray diffraction pattern from the crystallized molecule or molecular complex; applying at least a portion of the structure coordinates set forth in Table 1 to the x-ray diffraction pattern to generate a three-dimensional electron density map of at least a portion of the molecule or molecular complex whose structure is unknown.

In another aspect, the present invention provides a method for homology modeling an *S. aureus* NAD synthetase homolog including: aligning the amino acid sequence of an *S. aureus* NAD synthetase homolog with an amino acid sequence of *S. aureus* NAD synthetase (SEQ ID NO: 1) and incorporating the sequence of the *S. aureus* NAD synthetase homolog into a model of *S. aureus* NAD synthetase derived from structure coordinates set forth in Table 1 to yield a preliminary model of the *S. aureus* NAD synthetase homolog; subjecting the preliminary model to energy minimization to yield an energy minimized model; remodeling regions of the energy minimized model where stereochemistry restraints are violated to yield a final model of the *S. aureus* NAD synthetase homolog.

In another aspect, the present invention provides a computer-assisted method for identifying an inhibitor of *S. aureus* NAD synthetase activity including: supplying a computer modeling application with a set of structure coordinates of a molecule or molecular complex, the molecule or molecular complex including at least a portion of an *S. aureus* NAD synthetase or NAD synthetase-like substrate binding pocket, the substrate binding pocket including the amino acids listed in Table 3; supplying the computer modeling application with a set of structure coordinates of a chemical entity; and determining whether the chemical entity is an inhibitor expected to bind to or interfere with the molecule or molecular complex, wherein binding to or interfering with the molecule or molecular complex is indicative of potential inhibition of *S. aureus* NAD synthetase activity. Preferably the substrate binding pocket includes the amino acids listed in Table 3, the substrate binding pocket being defined by a set of points having a root mean square deviation of less than about 1.1 Å from points representing the backbone atoms of the amino acids as represented by structure coordinates listed in Table 1. Preferably determining whether the chemical entity is an inhibitor expected to bind to or interfere with the molecule or molecular complex includes performing a fitting operation between the chemical entity and a binding pocket of the molecule or molecular complex, followed by computationally analyzing the results of the fitting operation to quantify the association between the chemical entity and the binding pocket. Preferably the method further includes screening a library of chemical entities. Preferably the method further includes supplying or synthesizing the potential inhibitor, then assaying the potential inhibitor to determine whether it inhibits *S. aureus* NadE activity.

In another aspect, the present invention provides a computer-assisted method for designing an inhibitor of *S. aureus* NAD synthetase activity including: supplying a computer modeling application with a set of structure coordinates of a molecule or molecular complex, the molecule or molecular complex including at least a portion of an *S. aureus* NAD synthetase or NAD synthetase-like substrate binding pocket, the substrate binding pocket including the amino acids listed in Table 3; supplying the computer modeling application with a set of structure coordinates for a chemical entity; evaluating the potential binding interactions between the chemical entity and substrate binding pocket of the molecule or molecular complex; structurally modifying the chemical entity to yield a set of structure coordinates for a modified chemical entity; and determining whether the modified chemical entity is an inhibitor expected to bind to or interfere with the molecule or molecular complex, wherein binding to or interfering with the molecule or molecular complex is indicative of potential inhibition of *S. aureus* NAD synthetase activity. Preferably the substrate binding pocket includes the amino acids listed in Table 3, the substrate binding pocket being defined by a set of points having a root mean square deviation of less than about 1 Å from points representing the backbone atoms of the amino acids as represented by structure coordinates listed in Table 1. Preferably determining whether the modified chemical entity is an inhibitor expected to bind to or interfere with the molecule or molecular complex includes performing a fitting operation between the chemical entity and a binding pocket of the molecule or molecular complex, followed by computationally analyzing the results of the fitting operation to quantify the association between the chemical entity and the binding pocket. Preferably the set of structure coordinates for the chemical entity is obtained from a chemical fragment library. Preferably the method further includes supplying or synthesizing the potential inhibitor, then assaying the potential inhibitor to determine whether it inhibits *S. aureus* NadE activity.

In another aspect, the present invention provides a computer-assisted method for designing an inhibitor of *S. aureus* NAD synthetase activity de novo including: supplying a computer modeling application with a set of structure coordinates of a molecule or molecular complex, the molecule or molecular complex including at least a portion of an *S. aureus* NAD synthetase or NAD synthetase-like substrate binding pocket, wherein the substrate substrate binding pocket includes the amino acids listed in Table 3; computationally building a chemical entity represented by set of structure coordinates; and determining whether the chemical entity is an inhibitor expected to bind to or interfere with the molecule or molecular complex, wherein binding to or interfering with the molecule or molecular complex is indicative of potential inhibition of *S. aureus* NAD synthetase activity. Preferably the substrate binding pocket includes the amino acids listed in Table 3, the substrate binding pocket being defined by a set of points having a root mean square deviation of less than about 1.1 Å from points representing the backbone atoms of the amino acids as represented by structure coordinates listed in Table 1. Preferably determining whether the chemical entity is an inhibitor expected to bind to or interfere with the molecule or molecular complex includes performing a fitting operation between the chemical entity and a binding pocket of the molecule or molecular complex, followed by computationally analyzing the results of the fitting operation to quantify the association between the chemical entity and the binding pocket. Preferably the method further includes supplying or synthesizing the potential inhibitor, then assaying the potential inhibitor to determine whether it inhibits S. aureus NadE activity.

In another aspect, the present invention provides a method for making an inhibitor of S. aureus NadE activity, the method including chemically or enzymatically synthesizing a chemical entity to yield an inhibitor of S. aureus NadE activity, the chemical entity having been identified during a computer-assisted process including supplying a computer modeling application with a set of structure coordinates of a molecule or molecular complex, the molecule or molecular complex including at least a portion of at least one of a S. aureus NAD synthetase or NAD synthetase-like substrate binding pocket; supplying the computer modeling application with a set of structure coordinates of a chemical entity; and determining whether the chemical entity is expected to bind to or interfere with the molecule or molecular complex at a binding pocket, wherein binding to or interfering with the molecule or molecular complex is indicative of potential inhibition of S. aureus NadE activity.

In another aspect, the present invention provides a method for making an inhibitor of S. aureus NadE activity, the method including chemically or enzymatically synthesizing a chemical entity to yield an inhibitor of S. aureus NadE activity, the chemical entity having been designed during a computer-assisted process including supplying a computer modeling application with a set of structure coordinates of a molecule or molecular complex, the molecule or molecular complex including at least a portion of at least one of a S. aureus NAD synthetase or NAD synthetase-like substrate binding pocket; supplying the computer modeling application with a set of structure coordinates for a chemical entity; evaluating the potential binding interactions between the chemical entity and a binding pocket of the molecule or molecular complex; structurally modifying the chemical entity to yield a set of structure coordinates for a modified chemical entity; and determining whether the chemical entity is expected to bind to or interfere with the molecule or molecular complex at the binding pocket, wherein binding to or interfering with the molecule or molecular complex is indicative of potential inhibition of S. aureus NadE activity.

In another aspect, the present invention provides a method for making an inhibitor of S. aureus NadE activity, the method including chemically or enzymatically synthesizing a chemical entity to yield an inhibitor of S. aureus NadE activity, the chemical entity having been designed during a computer-assisted process including supplying a computer modeling application with a set of structure coordinates of a molecule or molecular complex, the molecule or molecular complex including at least a portion of at least one of a S. aureus NAD synthetase or NAD synthetase-like substrate binding pocket; computationally building a chemical entity represented by set of structure coordinates; and determining whether the chemical entity is expected to bind to or interfere with the molecule or molecular complex at a binding pocket, wherein binding to or interfering with the molecule or molecular complex is indicative of potential inhibition of S. aureus NadE activity.

In another aspect, the present invention provides inhibitors or compositions including inhibitors of S. aureus NAD synthetase activity identified, designed or made according to the methods of the present invention. Preferably the compositions are pharmaceutical compositions including the inhibitor or salt thereof and a pharmaceutically acceptable carrier.

In another aspect, the present invention provides a method for crystallizing an S. aureus NAD synthetase molecule or molecular complex. In one embodiment, the method includes: providing purified S. aureus NAD synthetase at a concentration of about 1 mg/ml to about 50 mg/ml; and crystallizing S. aureus NAD synthetase from a solution including about 5% by weight to about 50% by weight PEG and about 0% by weight to about 20% by weight DMSO.

In another embodiment, the method includes: providing purified S. aureus NAD synthetase at a concentration of about 1 mg/ml to about 50 mg/ml; and crystallizing S. aureus NAD synthetase from a solution including about 1% by weight to about 10% by weight PEG, about 0.1 M to about 5 M ammonium sulfate, and about 0% by weight to about 20% by weight DMSO, wherein the solution is buffered to a pH of about 6 to about 9.

In still another embodiment, the method includes: providing purified S. aureus NAD synthetase at a concentration of about 1 mg/ml to about 50 mg/ml; and crystallizing S. aureus NAD synthetase from a solution including about 5% by weight to about 50% by weight PEG and about 0% by weight to about 20% by weight DMSO, wherein the solution is buffered to a pH of about 8 to about 11.

In another aspect, the present invention provides a crystal of S. aureus NAD synthetase. Preferably the crystal has the monoclinic space group symmetry $P2_1$. Preferably the crystal includes a unit cell having dimensions of a, b, and c; wherein a is about 40 Å to about 60 Å, b is about 90 Å to about 120 Å, and c is about 80 Å to about 110 Å; and wherein $\alpha=\gamma=90°$ and $\beta$ is about 80° to about 120°. Preferably the crystal includes atoms arranged in a spatial relationship represented by the structure coordinates listed in Table 1. Preferably the crystal of has the amino acid sequence SEQ ID NO:1. Optionally at least one methionine may be replaced with selenomethionine.

TABLE 3

Residues within about 4 Å of the substrate binding pocket of S. aureus NadE

| Molecule #1 | LEU 47 | LEU 83 | GLU 165 | LEU 214 |
|---|---|---|---|---|
| | GLY 48 | PHE 132 | PHE 170 | HIS 260 |
| | ILE 49 | ASN 136 | TYR 171 | LYS 261 |
| | SER 50 | ARG 140 | THR 172 | TYR 266 |
| | SER 55 | ARG 142 | LYS 173 | |
| | VAL 81 | THR 160 | ASP 176 | |
| Molecule #2 | TYR 1035 | PHE 1147 | SER 1151 | ASP 1180 |

TABLE 4

Residues within about 7 Å of the substrate binding pocket of S. aureus NadE

| Molecule #1 | LEU 47 | GLN 88 | GLU 165 | GLU 215 |
|---|---|---|---|---|
| | GLY 48 | VAL 94 | GLY 169 | LEU 221 |
| | ILE 49 | ILE 111 | PHE 170 | ASP 223 |
| | SER 50 | PHE 132 | TYR 171 | ALA 226 |
| | GLY 51 | GLY 135 | THR 172 | TYR 231 |
| | GLY 52 | ASN 136 | LYS 173 | ILE 256 |
| | GLN 53 | ALA 139 | TYR 174 | ARG 257 |
| | ASP 54 | ARG 140 | GLY 175 | ASN 258 |
| | SER 55 | ARG 142 | ASP 176 | ALA 259 |
| | THR 56 | GLN 146 | GLY 177 | HIS 260 |
| | VAL 81 | VAL 158 | LYS 189 | LYS 261 |

TABLE 4-continued

Residues within about 7 Å of the substrate binding pocket of S. aureus NadE

|  | | | | |
|---|---|---|---|---|
|  | LYS 82 | GLY 159 | THR 211 | ALA 265 |
|  | LEU 83 | THR 160 | ALA 212 | TYR 266 |
|  | PRO 84 | ASP 161 | ASP 213 | TRP 271 |
|  | TYR 85 | HIS 162 | LEU 214 |  |
| Molecule #2 | TYR 1035 | GLN 1146 | SER 1151 | ALA 1179 |
|  | HIS 1039 | PHE 1147 | GLY 1155 | ASP 1180 |
|  | PHE 1041 | SER 1148 | ILE 1156 | ILE 1181 |
|  | ILE 1042 | ALA 1150 | VAL 1157 |  |

TABLE 5

Residues within about 10 Å of the substrate binding pocket of S. aureus NadE

| Molecule #1 | VAL 46 | VAL 94 | THR 160 | ASP 217 |
|---|---|---|---|---|
|  | LEU 47 | GLU 95 | ASP 161 | LYS 218 |
|  | GLY 48 | ALA 97 | HIS 162 | LEU 221 |
|  | ILE 49 | LEU 98 | ALA 164 | PRO 222 |
|  | SER 50 | ILE 101 | GLU 165 | ASP 223 |
|  | GLY 51 | VAL 107 | ASN 166 | GLU 224 |
|  | GLY 52 | THR 108 | THR 168 | ASP 225 |
|  | GLN 53 | VAL 109 | GLY 169 | ALA 226 |
|  | ASP 54 | ASN 110 | PHE 170 | LEU 227 |
|  | SER 55 | ILE 111 | TYR 171 | TYR 231 |
|  | THR 56 | THR 130 | THR 172 | HIS 254 |
|  | LEU 57 | ASP 131 | LYS 173 | TYR 255 |
|  | VAL 58 | PHE 132 | TYR 174 | ILE 256 |
|  | GLY 59 | GLN 133 | GLY 175 | ARG 257 |
|  | PHE 78 | LYS 134 | ASP 176 | ASN 258 |
|  | ILE 79 | GLY 135 | GLY 177 | ALA 259 |
|  | ALA 80 | ASN 136 | ALA 178 | HIS 260 |
|  | VAL 81 | GLU 137 | ALA 179 | LYS 261 |
|  | LYS 82 | LYS 138 | ILE 184 | ARG 262 |
|  | LEU 83 | ALA 139 | LYS 189 | GLU 263 |
|  | PRO 84 | ARG 140 | LYS 208 | LEU 264 |
|  | TYR 85 | GLU 141 | THR 209 | ALA 265 |
|  | GLY 86 | ARG 142 | PRO 210 | TYR 266 |
|  | VAL 87 | MET 143 | THR 211 | THR 267 |
|  | GLN 88 | VAL 145 | ALA 212 | THR 270 |
|  | LYS 89 | GLN 146 | ASP 213 | TRP 271 |
|  | ASP 90 | VAL 157 | LEU 214 | PRO 272 |
|  | ALA 91 | VAL 158 | GLU 215 |  |
|  | GLU 93 | GLY 159 | ASP 216 |  |
| Molecule #2 | PHE 1031 | LEU 1045 | ALA 1150 | GLY 1159 |
|  | TYR 1035 | VAL 1046 | SER 1151 | ALA 1178 |
|  | VAL 1036 | MET 1143 | ASN 1152 | ALA 1179 |
|  | SER 1038 | LYS 1144 | ARG 1153 | ASP 1180 |
|  | HIS 1039 | VAL 1145 | GLN 1154 | ILE 1181 |
|  | SER 1040 | GLN 1146 | GLY 1155 | ALA 1182 |
|  | PHE 1041 | PHE 1147 | ILE 1156 |  |
|  | ILE 1042 | SER 1148 | VAL 1157 |  |
|  | SER 1044 | ILE 1149 | VAL 1158 |  |

Definitions

Two crystallographic data sets (with structure factors F) are considered isomorphous if, after scaling, $$\frac{\Delta F}{F} = \frac{\sum |F_1 - F_2|}{\sum F_1}$$

is less than about 35% for the reflections between 8 Å and 4 Å.

Abbreviations

The following abbreviations are used throughout this disclosure:

*Staphylococcus aureus* (*S. aureus*).
Reduced nicotinamide adenine dinucleotide (NADH)
Oxidized nicotinamide adenine dinucleotide (NAD$^+$)
NAD synthetase (NadE)
Nicotinic acid mononucleotide (NAM)
Adenosine 5'-diphosphate (ADP).
Adenosine 5'-triphosphate (ATP).
Isopropylthio-β-D-galactoside (IPTG).
Dimethyl sulfoxide (DMSO).
Polyethylene glycol (PEG).
Multiple anomalous dispersion (MAD).

The following amino acid abbreviations are used throughout this disclosure:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE FIGURES

FIG. 9 illustrates the sequence alignment of *S. aureus* NAD synthetase (NadE, SEQ ID NO:1) and *B. subtilis* synthetase (NadE_BS, SEQ ID NO:2). Underlined blocks indicate identical residues while dark shaded blocks indicate similar residues.

DETAILED DESCRIPTION OF THE INVENTION

Table 1 lists the atomic structure coordinates for molecules of *S. aureus* NadE as derived by x-ray diffraction from a crystal of that complex. Column 2 lists a number for the atom in the structure. Column 3 lists the element whose coordinates are measured. The first letter in the column defines the element. Column 4 lists the type of amino acid. Column 5 lists a number for the amino acid in the structure. Columns 6–8 list the crystallographic coordinates X, Y, and Z respectively. The crystallographic coordinates define the atomic position of the element measured. Column 9 lists an occupancy factor that refers to the fraction of the molecules in which each atom occupies the position specified by the coordinates. A value of "1" indicates that each atom has the same conformation, i.e., the same position, in all molecules of the crystal. Column 10 lists a thermal factor "B" that measures movement of the atom around its atomic center.

Table 2 lists the structure factors and multiple anomalous dispersion phases for the crystal structure of *S. aureus* NadE. Columns 2–4 refer to the indices of the lattice planes h, k, and l, respectively. Column 5 refers to the structure factor (F) of the observed reflections (Fobs). Column 6 refers to the standard deviation (Sigma) for the observations. Column 7 refers to the test number. The set of reflections used for calculations of the free R-factor were those where test number=1.

NAD synthetase (NadE) from *Staphylococcus aureus* is an enzyme that utilizes $NH_3$ to catalyze the final reaction in the biosynthesis of NAD. NAD synthetase has been thought to be a homodimeric protein in solution consisting of two identical subunits of 32 kDa. The protein has been screened for crystallization conditions using several commercially available solution libraries which resulted in three unique crystallization hits. Subsequent expansion of the condition from Hampton Crystal Screen 1-Lite (Hampton Research, Laguna Niguel, Calif.) allowed growth of 200–400 µm crystals in less than 96 hours. Both the native and selenomethionine forms of the enzyme have been crystallized and diffract to at least 2.2 Å at the synchrotron.

The structure of *S. aureus* NAD synthetase (NadE) has been solved to 2.3 Å resolution by molecular replacement. The dimeric structure reveals a substrate channel at the interface of the two monomers. The binding pocket can accommodate the deamino-$NAD^+$ as well as the ATP substrates based on the analogous *B. subtilis* NadE structure. This provides the first high resolution structure of *S. aureus* NadE.

Figure 6:
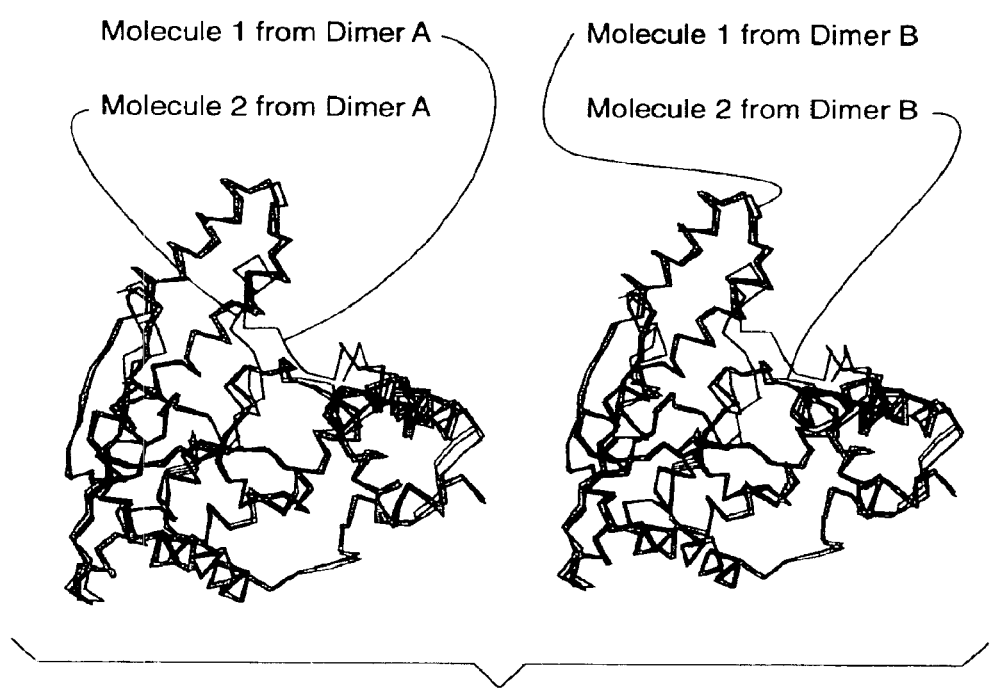
FIG. 6 depicts the superposition of the four *S. aureus* NadE molecules present in the asymmetric unit. Molecule 1 from dimer A served as the reference model. Molecule 2 from dimer A has a r.m.s. deviation of 0.68 Å from the C$_\alpha$ carbons of the reference model. Molecule 1 from dimer B has a r.m.s. deviation of 0.60 Å from the C$_\alpha$ carbons of the reference model. Molecule 2 from dimer has a r.m.s. deviation of 0.73 Å from the C$_\alpha$ carbons of the reference model.
Figure 7A:
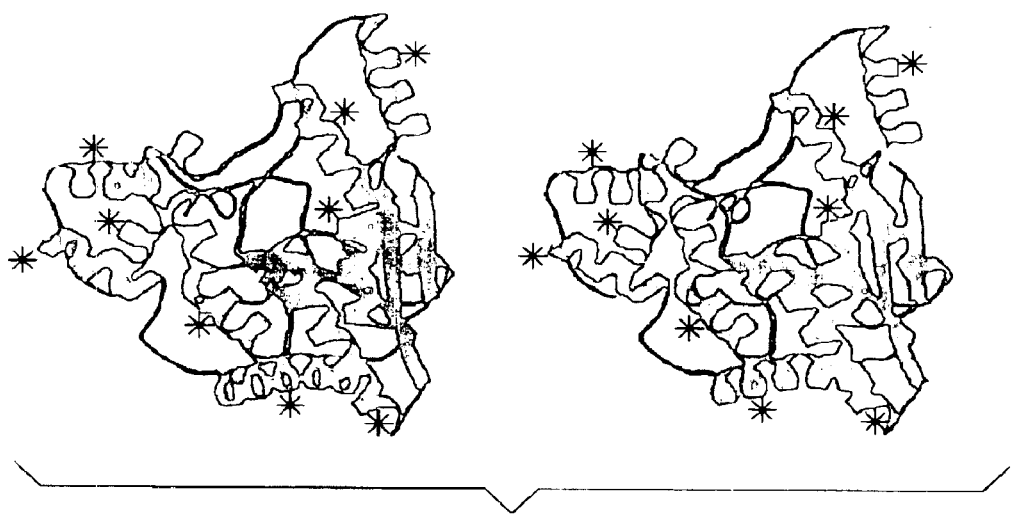
FIG. 7 depicts a) a stereo view of a NadE monomer (helices are starred and strands and loops are unlabeled); b) a topology diagram for *S. aureus* NadE; and c) the related *B. subtilis* NadE (figure based on Rizzi et al., *EMBO J.*, 15:5125–34 (1996)).

The *S. aureus* NadE structure contains five parallel β strands situated in a twisted β sheet surrounded by twelve α helices (FIGS. 6–7). The protein possesses a single domain and is similar to other α/β proteins which possess a six stranded dinucleotide binding Rossmann fold (Rossmann et al., Nature, 250:194–99 (1974)). The exception for NadE is that the sixth β strand does not exist and is replaced by several α helices. The dimensions of the monomer are 42 Å×42 Å×45 Å while the dimer has dimensions of 64 Å×37 Å×49 Å. The dimer interface forms a non-crystallographic 2-fold symmetry axis burying a surface area of 3300 $Å^2$.

Association of the two monomers into the active dimer is critical for the function of the enzyme since the two substrate channels are composed of residues from monomer A and monomer B.

Figure 8:
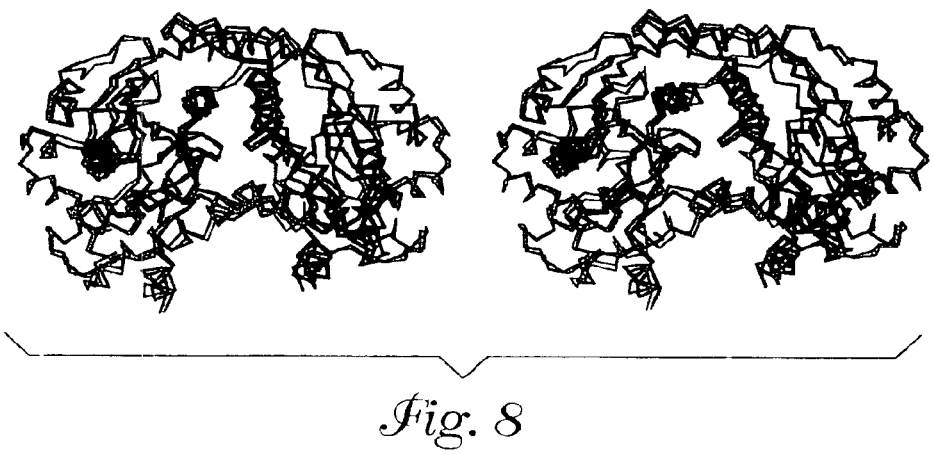
FIG. 8 depicts the superposition of *S. aureus* NadE dimer A (black) with *B. subtilis* NadE dimer (gray) (1nsy from the Protein Data Bank). The r.m.s. deviation between the C$_\alpha$ carbons of both dimers is 1.19 Å.

Superposition of the four *S. aureus* NadE molecules present in the asymmetric unit results in good agreement between all four molecules (r.m.s. deviations on alpha carbons from 0.60 Å to 0.73 Å, FIG. 6). A comparison of the *S. aureus* NadE dimer to the *B. subtilis* dimer used in the molecular replacement (the only NAD synthetase structure currently available from the Protein Data Bank) shown a r.m.s. deviation of 1.19 Å for all alpha carbons (FIG. 8). There is a one amino acid insertion in the loop between α2 and β1 in the *S. aureus* NadE structure when compared to the *B. subtilis* structure and a one amino acid deletion in the loop between α5 and α6 in the *S. aureus* NadE structure when compared to the *B. subtilis* structure. These differences result in only minor changes to the main chain location. These observations are consistent with the high homology between the two sequences (51% identical, 65% similar).

Crystalline Form(s) and Method of Making

Applicants have produced crystals comprising *S. aureus* NAD synthetase (and substrate or inhibitor), which are suitable for x-ray crystallographic analysis. Preferably, the crystals have one dimension of 0.15–0.8 mm, and more preferably dimensions of 0.15–0.8mm×0.2 mm×0.05–0.1 mm. The three-dimensional structure of *S. aureus* NAD synthetase or *S. aureus* NAD synthetase/ligand complex was solved using high resolution x-ray crystallography. Preferably, the crystal has the monoclinic space group symmetry $P2_1$. More preferably, the crystal comprises unit cells, each unit cell having dimensions of a, b, and c; wherein a is about 48 Å to about 53 Å, b is about 102 Å to about 113 Å, and c is about 87 Å to about 97 Å; and wherein α=γ=90°, β is about 80° to about 120°. The crystallized enzyme is a dimer and has two dimers in the asymmetric unit. Accordingly, one embodiment of the invention provides an *S. aureus* NAD synthetase or *S. aureus* NAD synthetase/ligand crystal.

The invention further includes *S. aureus* NAD synthetase crystals or *S. aureus* NAD synthetase/ligand crystals that are isomorphous with *S. aureus* NAD synthetase crystal characterized by a unit cell having the dimensions of a, b, and c; wherein a is about 48 Å to about 53 Å, b is about 102 Å to about 113 Å, and c is about 87 Å to about 97 Å; and wherein α=γ=90°, β is about 80° to about 120°.

X-Ray Crystallographic Analysis

Each of the constituent amino acids of *S. aureus* NadE is defined by a set of structure coordinates as set forth in Table 1. The term "structure coordinates" refers to Cartesian coordinates derived from mathematical equations related to the patterns obtained on diffraction of a monochromatic beam of x-rays by the atoms (scattering centers) of an *S. aureus* NadE complex in crystal form. The diffraction data are used to calculate an electron density map of the repeating unit of the crystal. The electron density maps are then used to establish the positions of the individual atoms of the *S. aureus* NadE protein or protein/ligand complex.

Slight variations in structure coordinates can be generated by mathematically manipulating the *S. aureus* NadE or *S. aureus* NadE/ligand structure coordinates. For example, the structure coordinates set forth in Table 1 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the *S. aureus* NadE or *S. aureus* NadE/ligand complex, as defined above, would not be expected to significantly alter the nature of ligands that could associate with the binding pockets. Thus, for example, a ligand that bound to the active site binding pocket of *S. aureus* NadE would also be expected to bind to or interfere with another binding pocket whose structure coordinates define a shape that falls within the acceptable error.

Binding Pockets/Active Sites/Other Structural Features

Figure 10:
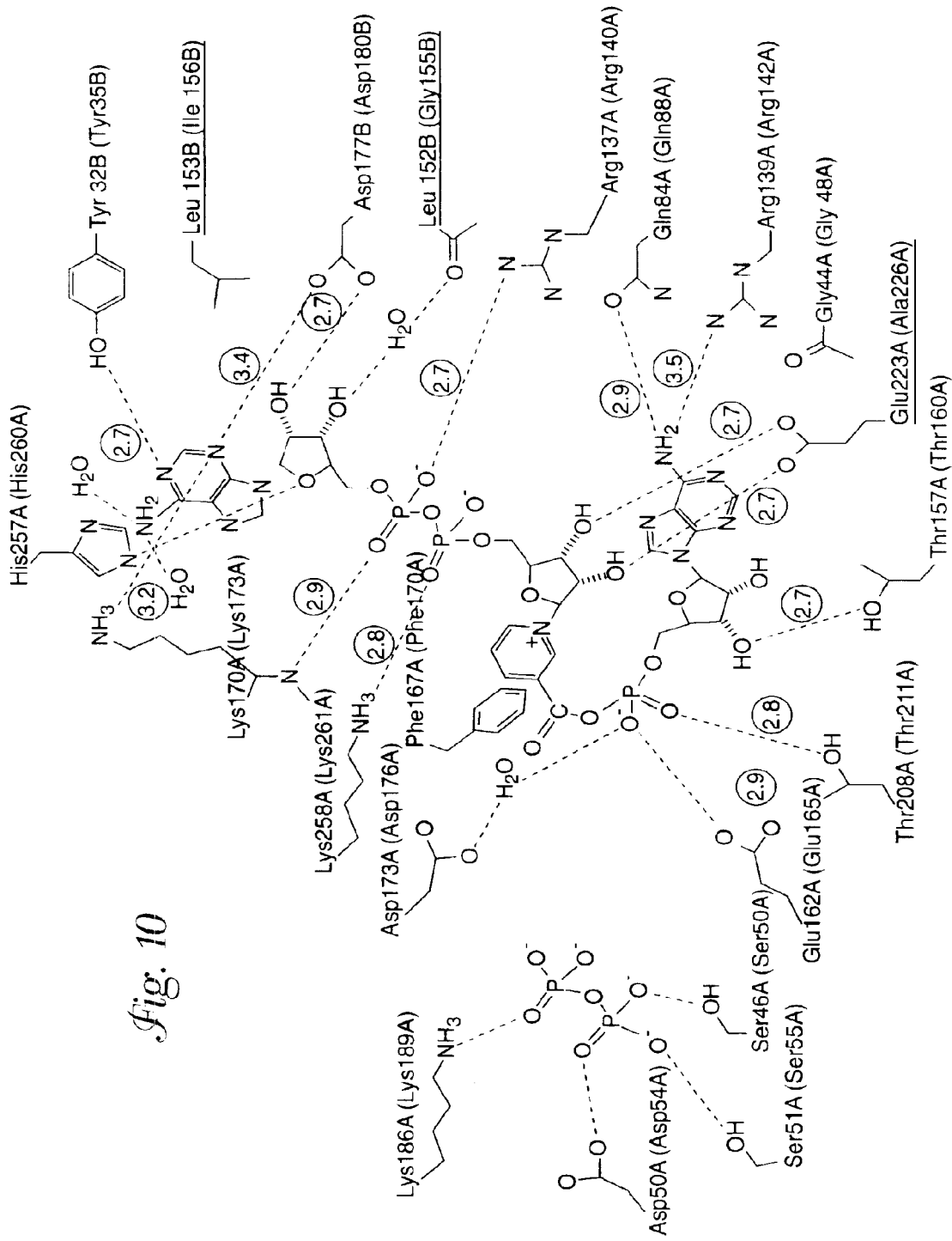
FIG. 10 is a schematic of ligand binding as observed in 2nsy (*B. subtilis* NadE with NAD-adenylate bound to the enzyme) with approximate distances in Å from one monomer shown as encircled numbers. Corresponding residues for *S. aureus* NadE are shown in parentheses. Underlined residues are those which are different in the two proteins. Molecule A is shown in black while molecule B is shown in gray.

The present invention has provided, for the first time, information about the shape and structure of the ligand binding pocket of *S. aureus* NAD synthetase. The active site of NadE is located at the interface between the two monomers drawing interactions from both the A molecule and B molecule to recognize the deamino-NAD substrate necessitating a dimeric structure to make active enzyme. The active site is an elongated channel on the order of 23 Å long and 5 Å wide. There is high conservation of residues within the active site of NAD synthetase between the *S. aureus* and *B. subtilis* proteins (FIG. 10). Of the twenty amino acids involved in direct or water mediated interactions with the NAD-adenylate intermediate as observed in the *B. subtilis* NadE co-crystal structure, only three changes exist in the *S. aureus* protein—Ile 156 in place of Leu 153 (conserved mutation), Gly 155 in place of Leu 152 (conserved interaction with main chain carbonyl), and Ala 226 in place of Glu 223 (a substantial mutation). Analysis of the *S. aureus* NadE structure does not reveal an obvious replacement for the Glu 223 interaction with the ribose hydroxyls of the AMP moiety. It is not clear at this time how the enzyme interacts with this portion of the ATP substrate whether through water mediated contacts or another amino acid. A specific comparison of the binding interactions between the *B. subtilis* and *S. aureus* enzymes must await a co-crystal of *S. aureus* NadE with ATP and/or NAD$^+$. In general, the cavity is quite similar between the unbound *S. aureus* structure and the bound *B. subtilis* structure (FIG. 11), although there will need to be measurable movement of the main chain in the region of residues 173–179 in order to facilitate optimal interaction with the substrates (FIG. 12).

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations helps lead to the design of drugs having more favorable associations with their target, and thus improved biological effects. Therefore, this information is valuable in designing potential inhibitors of *S. aureus* NAD synthetase-like binding pockets, as discussed in more detail below.

The term "binding pocket" (or active site), as used herein, refers to a region of a molecule or molecular complex, that, as a result of its shape, favorably associates with another chemical entity or compound. The binding pocket of *S. aureus* NAD synthetase preferably includes the amino acids listed in Table 3; more preferably the amino acids listed in Table 4; and most preferably the amino acids listed in Table 5, corresponding to the structure coodinates listed in Table 1. It will be readily apparent to those of skill in the art that the numbering of amino acids in other isoforms of *S. aureus* NAD synthetase may be different than that of *S. aureus* NAD synthetase isolated from *E. coli*. In another alternative, the binding pocket of *S. aureus* NAD synthetase may be defined by those amino acids whose backbone atoms are situated within about 4 Å, more preferably within about 7 Å, most preferably within about 10 Å, of one or more constituent atoms of a bound substrate or inhibitor, as determined from the structure coordinates in Table 1. Yet another way of defining the binding pocket of *S. aureus* NAD synthetase is in terms of pairwise interatomic distances.

The amino acid constituents of an *S. aureus* NAD synthetase binding pocket as defined herein, as well as selected constituent atoms thereof, are positioned in three dimensions in accordance with the structure coordinates listed in Table 1. In one aspect, the structure coordinates defining the binding pocket of *S. aureus* NAD synthetase include structure coordinates of all atoms in the constituent amino acids; in another aspect, the structure coordinates of the binding pocket include structure coordinates of just the backbone atoms of the constituent atoms.

The term "*S. aureus* NAD synthetase-like binding pocket" refers to a portion of a molecule or molecular complex whose shape is sufficiently similar to at least a portion of the active site binding pocket of *S. aureus* NAD synthetase as to be expected to bind related ligands. A structurally equivalent binding pocket is defined by a root mean square deviation from the structure coordinates of the backbone atoms of the amino acids that make up the binding pockets in *S. aureus* NAD synthetase (as set forth in Table 1) of at most about 1.1 Å. How this calculation is obtained is described below.

The term "associating with" refers to a condition of proximity between a chemical entity or compound, or portions thereof, and an *S. aureus* NAD synthetase molecule or portions thereof. The association may be non-covalent, wherein the juxtaposition is energetically favored by hydrogen bonding, van der Waals forces, or electrostatic interactions, or it may be covalent.

Accordingly, the invention thus provides molecules or molecular complexes comprising an *S. aureus* NAD synthetase binding pocket or *S. aureus* NAD synthetase-like binding pocket, as defined by the sets of structure coordinates described above.

Three-Dimensional Configurations

The structure coordinates generated for *S. aureus* NadE or the *S. aureus* NadE/ligand complex or one of its binding pockets shown in Table 1 define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes a scalable three-dimensional configuration of points derived from the structure coordinates of at least a portion of an *S. aureus* NadE molecule or molecular complex, as shown in Table 1, as well as structurally equivalent configurations, as described below. Preferably, the scalable three-dimensional configuration includes points derived from structure coordinates representing the locations of a plurality of the amino acids defining the *S. aureus* NadE binding pocket. In one embodiment, the scalable three-dimensional configuration includes points derived from structure coordinates representing the locations the backbone atoms of a plurality of amino acids defining the *S. aureus* NadE binding pocket, preferably the amino acids listed in Table 3; in another embodiment, the scalable three-dimensional configuration includes points derived from structure coordinates representing the locations of the side chain and the backbone atoms (other than hydrogens) of a plurality of the amino acids defining the *S. aureus* NadE binding pocket, preferably the amino acids listed in Table 3.

Likewise, the invention also includes the scalable three-dimensional configuration of points derived from structure coordinates of molecules or molecular complexes that are structurally homologous to *S. aureus* NadE, as well as structurally equivalent configurations. Structurally homologous molecules or molecular complexes are defined below. Advantageously, structurally homologous molecules can be identified using the structure coordinates of *S. aureus* NadE (Table 1) according to a method of the invention.

The configurations of points in space derived from structure coordinates according to the invention can be visualized as, for example, a holographic image, a stereodiagram, a model or a computer-displayed image, and the invention thus includes such images, diagrams or models.

Structurally Equivalent Crystal Structures

Various computational analyses can be used to determine whether a molecule or the binding pocket portion thereof is "structurally equivalent," defined in terms of its three-dimensional structure, to all or part of *S. aureus* NadE or its binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, Ca, C, and O) for all conserved residues between the two structures being compared. A conserved residue is defined as a residue that is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or binding pocket thereof, or any portion thereof, that has a root mean square deviation of conserved residue backbone atoms (N, Ca, C, O) of less than about 1.1 Å, when superimposed on the relevant backbone atoms described by the reference structure coordinates listed in Table 1, is considered "structurally equivalent" to the reference molecule. That is to say, the crystal structures of those portions of the two molecules are substantially identical, within acceptable error. Particularly preferred structurally equivalent molecules or molecular complexes are those that are defined by the entire set of structure coordinates in Table 1, ±a root mean square deviation from the conserved backbone atoms of those amino acids of not more than 1.1 Å. More preferably, the root mean square deviation is less than about 1.0 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of *S. aureus* NadE or a binding pocket portion thereof, as defined by the structure coordinates of *S. aureus* NadE described herein.

Machine Readable Storage Media

Transformation of the structure coordinates for all or a portion of *S. aureus* NadE or the *S. aureus* NadE/ligand complex or one of its binding pockets, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium comprising a data storage material encoded with machine readable data which, when using a machine programmed with instructions for using said data, is capable of displaying a graphical three-dimensional representation of any of the molecule or molecular complexes of this invention that have been described above. In a preferred embodiment, the machine-readable data storage medium comprises a data storage material encoded with machine readable data which, when using a machine programmed with instructions for using said data, is capable of displaying a graphical three-dimensional representation of a molecule or molecular complex comprising all or any parts of an *S. aureus* NadE binding pocket or an *S. aureus* NadE-like binding pocket, as defined above. In another preferred embodiment, the machine-readable data storage medium is capable of displaying a graphical three-dimensional representation of all the amino acids of a molecule or molecular complex defined by the structure coordinates in Table 1 ±a root mean square deviation from the backbone atoms of said amino acids of not more than 1.1 Å.

In an alternative embodiment, the machine-readable data storage medium comprises a data storage material encoded with a first set of machine readable data which comprises the Fourier transform of the structure coordinates set forth in Table 1, and which, when using a machine programmed with instructions for using said data, can be combined with a second set of machine readable data comprising the x-ray diffraction pattern of a molecule or molecular complex to determine at least a portion of the structure coordinates corresponding to the second set of machine readable data.

For example, a system for reading a data storage medium may include a computer comprising a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding pocket of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Structurally Homologous Molecules, Molecular Complexes, and Crystal Structures

The structure coordinates set forth in Table 1 can be used to aid in obtaining structural information about another crystallized molecule or molecular complex. A "molecular complex" means a protein in covalent or non-covalent association with a chemical entity or compound. The method of the invention allows determination of at least a portion of the three-dimensional structure of molecules or molecular complexes which contain one or more structural features that are similar to structural features of *S. aureus* NadE. These molecules are referred to herein as "structurally homologous" to *S. aureus* NadE. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al, *FEMS Microbiol Lett* 174, 247–50 (1999), and available from the world wide web at ncbi.nlm.nih.gov/gorf/b12.html. Preferably, the default values for all BLAST 2 search parameters are used, including matrix=BLOSUM62; open gap penalty=11, extension gap penalty=1, gapx_dropoff= 50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with the amino acid sequence of *S. aureus* NadE (SEQ ID NO:1). More preferably, a protein that is structurally homologous to *S. aureus* NadE includes at least one contiguous stretch of at least 50 amino acids that shares at least 80% amino acid sequence identity with the analogous portion of *S. aureus* NadE. Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown comprising the steps of:

(a) crystallizing the molecule or molecular complex of unknown structure;

(b) generating an x-ray diffraction pattern from said crystallized molecule or molecular complex; and (c) applying at least a portion of the structure coordinates set forth in Table 1 to the x-ray diffraction pattern to generate a three-dimensional electron density map of the molecule or molecular complex whose structure is unknown.

By using molecular replacement, all or part of the structure coordinates of *S. aureus* NadE or the *S. aureus* NadE/ ligand complex as provided by this invention (and set forth in Table 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of *S. aureus* NadE or the *S. aureus* NadE/ligand complex according to Table 1 within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions," in *Meth. Enzymol.*, 115, pp. 55–77 (1985); M. G. Rossman, ed., "The Molecular Replacement Method," *Int. Sci. Rev. Ser.*, No. 13, Gordon & Breach, New York (1972)).

Structural information about a portion of any crystallized molecule or molecular complex that is sufficiently structurally homologous to a portion of *S. aureus* NadE can be resolved by this method. In addition to a molecule that shares one or more structural features with *S. aureus* NadE as described above, a molecule that has similar bioactivity, such as the same catalytic activity, substrate specificity or ligand binding activity as *S. aureus* NadE, may also be sufficiently structurally homologous to *S. aureus* NadE to permit use of the structure coordinates of *S. aureus* NadE to solve its crystal structure.

In a preferred embodiment, the method of molecular replacement is utilized to obtain structural information about a molecule or molecular complex, wherein the molecule or molecular complex comprises at least one *S. aureus* NadE subunit or homolog. A "subunit" of *S. aureus* NadE is an *S. aureus* NadE molecule that has been truncated at the N-terminus or the C-terminus, or both. In the context of the present invention, a "homolog" of *S. aureus* NadE is a protein that contains one or more amino acid substitutions, deletions, additions, or rearrangements with respect to the amino acid sequence of *S. aureus* NadE, but that, when folded into its native conformation, exhibits or is reasonably expected to exhibit at least a portion of the tertiary (three-dimensional) structure of *S. aureus* NadE. For example, structurally homologous molecules can contain deletions or additions of one or more contiguous or noncontiguous amino acids, such as a loop or a domain. Structurally homologous molecules also include "modified" *S. aureus* NadE molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A heavy atom derivative of *S. aureus* NadE is also included as an *S. aureus* NadE homolog. The term "heavy atom derivative" refers to derivatives of *S. aureus* NadE produced by chemically modifying a crystal of *S. aureus* NadE. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (T. L. Blundell and N. L. Johnson, *Protein Crystallography*, Academic Press (1976)).

Because *S. aureus* NadE can crystallize in more than one crystal form, the structure coordinates of *S. aureus* NadE as provided by this invention are particularly useful in solving the structure of other crystal forms of *S. aureus* NadE or *S. aureus* NadE complexes.

The structure coordinates of *S. aureus* NadE in Table 1 are also particularly useful to solve the structure of crystals of *S. aureus* NadE homologs, *S. aureus* NadE mutants, or *S. aureus* NadE homologs co-complexed with a variety of chemical entities. This approach enables the determination of the optimal sites for interaction between chemical entities, including candidate *S. aureus* NadE inhibitors and *S. aureus* NadE. Potential sites for modification within the various binding site of the molecule can also be identified. This information provides an additional tool for determining the most efficient binding interactions, for example, increased hydrophobic interactions, between *S. aureus* NadE and a chemical entity. For example, high resolution x-ray diffraction data collected from crystals exposed to different types of solvent allows the determination of where each type of solvent molecule resides. Small molecules that bind tightly to those sites can then be designed and synthesized and tested for their *S. aureus* NadE inhibition activity.

All of the complexes referred to above may be studied using well-known x-ray diffraction techniques and may be refined versus 1.5–3 Å resolution x-ray data to an R value of about 0.20 or less using computer software, such as X-PLOR (Yale University, (1992), distributed by Molecular Simulations, Inc.; see, e.g., Blundell & Johnson, supra; *Meth. Enzymol.*, Vol. 114 & 115, H. W. Wyckoff et al., eds., Academic Press (1985)). This information may thus be used to optimize known *S. aureus* NadE inhibitors, and more importantly, to design new *S. aureus* NadE inhibitors.

The invention also includes the unique scalable three-dimensional configuration defined by a set of points defined by the structure coordinates for a molecule or molecular complex structurally homologous to *S. aureus* NadE as determined using the method of the present invention, structurally equivalent configurations, and magnetic storage media comprising such set of structure coordinates.

Further, the invention includes structurally homologous molecules as identified using the method of the invention.

Homology Modeling

Using homology modeling, a computer model of an *S. aureus* NadE homolog can be built or refined without crystallizing the homolog. First, a preliminary model of the *S. aureus* NadE homolog is created by sequence alignment with *S. aureus* NadE, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. Where the *S. aureus* NadE homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement comprising molecular dynamics calculations.

Rational Drug Design

Computational techniques can be used to screen, identify, select and design chemical entities capable of associating with *S. aureus* NadE or structurally homologous molecules. Knowledge of the structure coordinates for *S. aureus* NadE permits the design and/or identification of synthetic compounds and/or other molecules which have a shape complementary to the conformation of the *S. aureus* NadE binding site. In particular, computational techniques can be used to identify or design chemical entities, such as inhibitors, agonists and antagonists, that associate with an *S. aureus* NadE binding pocket or an *S. aureus* NadE-like binding pocket. Inhibitors may bind to or interfere with all or a portion of the active site of *S. aureus* NadE, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block *S. aureus* NadE activity and, thus, result in inhibition of growth or death of the bacteria. Structure-activity data for analogs of ligands that bind to or interfere with *S. aureus* NadE or *S. aureus* NadE-like binding pockets can also be obtained computationally.

The term "chemical entity," as used herein, refers to chemical compounds, complexes of two or more chemical compounds, and fragments of such compounds or complexes. Chemical entities that are determined to associate with *S. aureus* NadE are potential drug candidates. Data stored in a machine-readable storage medium that is capable of displaying a graphical three-dimensional representation of the structure of *S. aureus* NadE or a structurally homologous molecule, as identified herein, or portions thereof may thus be advantageously used for drug discovery. The structure coordinates of the chemical entity are used to generate a three-dimensional image that can be computationally fit to the three-dimensional image of *S. aureus* NadE or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with *S. aureus* NadE or a structurally homologous molecule, particularly with an *S. aureus* NadE binding pocket or *S. aureus* NadE-like binding pocket. The method of drug design thus includes computationally evaluating the potential of a selected chemical entity to associate with any of the molecules or molecular complexes set forth above. This method comprises the steps of: (a) employing computational means to perform a fitting operation between the selected chemical entity and a binding pocket of the molecule or molecular complex; and (b) analyzing the results of said fitting operation to quantify the association between the chemical entity and the binding pocket.

In another embodiment, the method of drug design involves computer-assisted design of chemical entities that associate with *S. aureus* NadE, its homologs, or portions thereof. Chemical entities can be designed in a step-wise fashion, one fragment at a time, or may be designed as a whole or "de novo."

To be a viable drug candidate, the chemical entity identified or designed according to the method must be capable of structurally associating with at least part of an *S. aureus* NadE or *S. aureus* NadE-like binding pockets, and must be able, sterically and energetically, to assume a conformation that allows it to associate with the *S. aureus* NadE or *S. aureus* NadE-like binding pocket. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the binding pocket, and the spacing between various functional groups of an entity that directly interact with the *S. aureus* NadE-like binding pocket or homologs thereof.

Optionally, the potential binding of a chemical entity to an *S. aureus* NadE or *S. aureus* NadE-like binding pocket is analyzed using computer modeling techniques prior to the actual synthesis and testing of the chemical entity. If these computational experiments suggest insufficient interaction and association between it and the *S. aureus* NadE or *S. aureus* NadE-like binding pocket, testing of the entity is obviated. However, if computer modeling indicates a strong interaction, the molecule may then be synthesized and tested for its ability to bind to or interfere with an *S. aureus* NadE or *S. aureus* NadE-like binding pocket. Binding assays to determine if a compound actually binds to *S. aureus* NadE can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One skilled in the art may use one of several methods to screen chemical entities or fragments for their ability to associate with an *S. aureus* NadE or *S. aureus* NadE-like binding pocket. This process may begin by visual inspection of, for example, an *S. aureus* NadE or *S. aureus* NadE-like binding pocket on the computer screen based on the *S. aureus* NadE structure coordinates in Table 1 or other coordinates which define a similar shape generated from the machine-readable storage medium. Selected fragments or chemical entities may then be positioned in a variety of orientations, or docked, within the binding pocket. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (P. J. Goodford, *J. Med. Chem.* 28:849–857 (1985); available from Oxford University, Oxford, UK); MCSS (A. Miranker et al., *Proteins: Struct. Funct. Gen.*, 11:29–34 (1991); available from Molecular Simulations, San Diego, Calif.); AUTODOCK (D. S. Goodsell et al., *Proteins: Struct. Funct. Genet.* 8:195–202 (1990); available from Scripps Research Institute, La Jolla, Calif.); and DOCK (I. D. Kuntz et al., *J. Mol. Biol.* 161:269–288 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of *S. aureus* NadE. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (P. A. Bartlett et al., in *Molecular Recognition: Chemical and Biological Problems*," Special Publ., Royal Chem. Soc., 78:182–196 (1989); G. Lauri et al., *J. Comput. Aided Mol. Des.* 8:51–66 (1994); available from the University of California, Berkeley, Calif.); 3D database systems such as ISIS (available from MDL Information Systems, San Leandro, Calif., reviewed in Y. C. Martin, *J. Med. Chem.* 35:2145–2154 (1992)); and HOOK (M. B. Eisen et al., *Proteins: Struc., Funct., Genet.* 19:199–221 (1994); available from Molecular Simulations, San Diego, Calif.).

*S. aureus* NadE binding compounds may be designed "de novo" using either an empty binding site or optionally including some portion(s) of a known inhibitor(s). There are many de novo ligand design methods including, without limitation, LUDI (H.-J. Bohm, *J. Comp. Aid. Molec. Design.* 6:61–78 (1992); available from Molecular Simulations Inc., San Diego, Calif.), LEGEND (Y. Nishibata et al., *Tetrahedron*, 47:8985–8990 (1991); available from Molecular Simulations Inc., San Diego, Calif.); LeapFrog (available from Tripos Associates, St. Louis, Mo.); and SPROUT (V. Gillet et al., *J. Comput. Aided Mol. Design* 7:127–153 (1993); available from the University of Leeds, UK).

Once a compound has been designed or selected by the above methods, the efficiency with which that entity may bind to or interfere with an *S. aureus* NadE or *S. aureus* NadE-like binding pocket may be tested and optimized by computational evaluation. For example, an effective *S. aureus* NadE or *S. aureus* NadE-like binding pocket inhibitor must preferably demonstrate a relatively small difference in energy between its bound and free states (i.e., a small deformation energy of binding). Thus, the most efficient *S. aureus* NadE or *S. aureus* NadE-like binding pocket inhibitors should preferably be designed with a deformation energy of binding of not greater than about 10 kcal/mole; more preferably, not greater than 7 kcal/mole. *S. aureus* NadE or *S. aureus* NadE-like binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to or interfering with an *S. aureus* NadE or *S. aureus* NadE-like binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. (1995)); AMBER, version 4.1 (P. A. Kollman, University of California at San Francisco, (1995)); QUANTA/CHARMM (Molecular Simulations, Inc., San Diego, Calif. (1995)); Insight II/Discover (Molecular Simulations, Inc., San Diego, Calif. (1995)); DelPhi (Molecular Simulations, Inc., San Diego, Calif. (1995)); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach encompassed by this invention is the computational screening of small molecule databases for chemical entities or compounds that can bind in whole, or in part, to a *S. aureus* NadE or *S. aureus* NadE-like binding pocket. In this screening, the quality of fit of such entities to the binding site may be judged either by shape complementarity or by estimated interaction energy (E. C. Meng et al., *J. Comp. Chem.*, 13, pp. 505–524 (1992)).

This invention also enables the development of chemical entities that can isomerize to short-lived reaction intermediates in the chemical reaction of a substrate or other compound that binds to or with *S. aureus* NadE. Time-dependent analysis of structural changes in *S. aureus* NadE during its interaction with other molecules is carried out. The reaction intermediates of *S. aureus* NadE can also be deduced from the reaction product in co-complex with *S. aureus* NadE. Such information is useful to design improved analogs of known *S. aureus* NadE inhibitors or to design novel classes of inhibitors based on the reaction intermediates of the *S. aureus* NadE and inhibitor co-complex. This provides a novel route for designing *S. aureus* NadE inhibitors with both high specificity and stability.

Yet another approach to rational drug design involves probing the *S. aureus* NadE crystal of the invention with molecules comprising a variety of different functional groups to determine optimal sites for interaction between candidate *S. aureus* NadE inhibitors and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their hepes protease inhibitor activity (J. Travis, *Science*, 262:1374 (1993)).

In a related approach, iterative drug design is used to identify inhibitors of *S. aureus* NadE. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

Pharmaceutical Compositions

Pharmaceutical compositions of this invention comprise an inhibitor of *S. aureus* NadE activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intra-articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the S. aureus NadE inhibitory compounds described herein are useful for the prevention and treatment of S. aureus NadE mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In order that this invention be more fully understood, the following examples are set forth. These examples are for the purpose of illustration only and are not to be construed as limiting the scope of the invention in any way.

EXAMPLES

Example 1

Analysis of the Structure of S. aureus NadE

A. Expression, Purification and Crystallization

NAD synthetase was expressed from recombinant Escherichia coli culture TU576 (M15 pQE60-NAD synthetase), an expression strain constructed by Human Genome Sciences. A single colony was picked from a fresh streak plate to inoculate NS86 seed medium, grown to ~1 $A_{550}$ and frozen ampoules (20% glycerol was added as a cryoprotectant) were prepared. Ampoules were stored in the vapor phase of liquid nitrogen.

To prepare the seed, cells were grown in NS86 medium (2.6 g/L $K_2HPO_4$, 10.9 g/L $NaNH_4HPO_4$-$4H_2O$, 2.1 g/L citric acid, 0.67 g/L $(NH_4)_2SO_4$, 0.25 g/L $MgSO_4$-$7H_2O$, 10.4 g/L yeast extract and 5 g/L glycerol) containing both ampicillin (100 micrograms/mL) and kanamycin (25 micrograms/mL). Shake flask medium was MIM (32 g/L tryptone, 20 g/L yeast extract, 6 g/L $Na_2HPO_4$, 3 g/L $KH_2PO_4$, 0.5 g/L NaCl, and 1 g/L $NH_4Cl$) containing ampicillin and kanamycin (100 and 25 g/mL, respectively). Seeds were prepared by the inoculation of 0.1 mL thawed ampoule contents into 50 milliliters of NS86 medium and grown overnight at 30° C. Flasks (4000-mL volume) containing 750 milliliters MIM medium were inoculated at $A_{550}$=0.1. Cells were grown at 30° C., induced at a density of $A_{550}$=1.0 by the addition of 1 mM IPTG and harvested at 2.5 hours post-induction by centrifugation.

Cell paste was suspended in lysis buffer [50 mM Tris, pH 8.0, 5 mM β-mercaptoethanol, 1.8 g/L lysozyme, 100 mg/L DNAse, Complete™ protease inhibitor tablets (1 tablet/50 mL, Boehringer Mannheim)]. Cell suspensions were kept on ice for ~2 hours and homogenized using a Tissuemizer every 15–20 minutes. At the end of 2 hours, cell lysates were clarified by centrifugation at 17,211-xg (12,000 rpm, SS34 rotor) at 4° C. for 30 minutes. NaCl and imidazole were added to the clarified lysates to final concentrations of 0.5 M and 20 mM, respectively.

Immobilized metal affinity chromatography was conducted as follows. Clarified cell lysates were loaded onto a 50 mL column (2.5 cm id) of $Ni^{+2}$-NAT agarose (Qiagen) which had been pre-washed with water and equilibrated with buffer (50 mM Tris, 0.5 M NaCl, pH 8.0, 5 mM β-mercaptoethanol) containing 20 mM imidazole, after which the column was washed with additional buffer until the absorbance returned to baseline. The column then was eluted with buffer containing 50 mM imidazole, followed by buffer containing 250 mM imidazole, during which the column eluate was collected in 1 minute fractions (~2.5 mL). Throughout the chromatography, the flow rate was 2.5 mL/min; the absorbance was monitored at 278 nm. IMAC-purified NAD synthetase was dialyzed at 4° C. against 50 mM Tris, pH 8.0, 5 mM β-mercaptoethanol and loaded onto a 20 mL column (2.5 cm id) of Source Q (Amersham-Pharmacia Biotech) which had been equilibrated with the same buffer. Following load, the column was washed with the equilibration buffer and then eluted with a linear gradient from equilibration buffer to buffer plus 250 mM NaCl, over 10 column volumes. The column was washed and eluted at 2.5 mL/min; the eluate was monitored at 278 nm. The total protein concentration of lysates, column fractions, and product pools was determined using Coomassie blue protein reagent from Pierce Chemical Co.

SDS-PAGE was performed according to known methods (Laemmli, Nature, 227:680–85 (1970)) using reducing conditions. Tris-Glycine 10"20% polyacrylamide gradient gels were purchased from Owl Separation Systems. Electrophoresis was conducted at 30 mA (constant current) for a single gel or 60 mA for two gels. Gels were stained for 30 minutes at room temperature with 0.25% (w/v) Coomassie Blue G-250 in 20% acetic acid/80% water. Gels were destained for 30 minutes in 50% methanol/10% acetic acid/40% water, followed by destaining and storage in 5% methanol/7% acetic acid/88% water. Low molecular weight protein standards were purchased from Novex; 20 μL of standard was loaded per gel lane. Protein samples were diluted to 0.2 μg/μL; 20 μL was loaded per well.

For the preparation of selenomethionine NadE, the expression strain was inoculated into M9 glucose medium containing ampicillin, kanamycin and thiamin at 100, 30 and 3 mg/L, respectively. One hundred-mL volumes of medium were contained in 500-mL wide mouth fermentation flasks which were incubated overnight at 30° C. with agitation at 200 rpm. These cultures were washed once, resuspended in an equal volume of fresh M9 and used as the seed inoculum for the production fermentation at a 4% rate. The production fermentation was carried out in the same medium using the identical fermentation conditions for about 4 hours when the turbidity at 600 nm was equal to about 0.5 unit. At this point, a mixture of amino acids including DL-Se-methionine was added to down regulate methionine biosynthesis. The mixture contained L-lysine, L-threonine, L-phenylalanine and DL-Se-methionine each at a concentration of 120 mg/L with L-valine, L-leucine and L-isoleucine each at a concentration of 60 mg/L. Fermentation was continued for an additional 15 min when IPTG was added to a final concentration of 1 mM. The fermentation was continued for an additional 2.5 hr (turbidity at 600 nm=1.5) when harvest was carried out by centrifugation. Two to four liter fermentation volumes were attained using multiple shake flasks.

The purified protein was determined to be >96% pure by SDS-PAGE. The sample was received in 25 mM Tris, pH 8.0, 5 mM β-mercaptoethanol (BME) as requested. BME was added to prevent loss of activity during storage (Zalkin, *Methods Enzymol.*, 113:297–302 (1985)). This buffer system is amenable to crystallization, therefore no buffer exchanges were necessary. The protein was directly concentrated to approx. 20 mg/mL using a pretreated Ultrafree-4 10,000 MWCO concentrator (Millipore). Concentration determination was done by concentration factors based on the original Bradford assay results. Amino acid analysis indicated that the concentration was actually 15 mg/mL, this is a 24% decrease from the earlier calculation. Freshly prepared sample was split into 50 μL aliquots, flash frozen in liquid nitrogen, and stored at −80° C. NAD synthetase was screened using the hanging drop method, in 24 well VDX plates (Hampton Research, Laguna Niguel, Calif.). The crystallization library consists of Hampton Research Crystal Screen I, Crystal Screen II, and Crystal Screen I- Lite (all available from Hampton Research, Laguna Niguel, Calif.) and Wizard I, Wizard II, Cryo I, and Cryo II (all available from Emerald Biostructures, Inc., Bainbridge Island, Wash.). NAD synthetase was screened in all conditions, with hits in Hampton Crystal Screen 1-Lite/43 (15% PEG 1,500), Hampton Crystal Screen 1/39 (2% PEG 400, 2.0 M Ammonium Sulfate, 0.1 M Na Hepes pH 7.5), and Wizard 1/41 (30% PEG-3000, CHES pH 9.5).

The largest, most easily reproducible crystals occurred in 15% PEG 1500. Subsequent expansion around this condition revealed the following: pH, concentration of protein, concentration and grade of PEG solutions, and the presence of salts restrict crystallization of this protein. Salts stabilize the protein, making it more difficult to bring out of solution. A limited biochemical profile has been obtained, with dynamic light scattering and gel filtration experiments confirming the presence of a dimer in solution. Crystallization solutions were 0.5 mL in the well. 1 μL well+1 μL protein drops were placed on siliconized coverslips, then suspended over the well solution. Growth of crystals occurred within 96 hours. These were protein crystals, but the morphology was of thin, spade or feather-like plates. Refinement of this condition showed that crystals could be obtained from 16–22% PEG 1500. During crystallization of this protein, precipitate, microcrystals and medium to large size crystals were observed. Several attempts to introduce pH buffers into this system invariably yielded poor crystals or precipitated protein. Buffer exchanging the protein solution into 100 mM Tris, 5 mM β-mercaptoethanol, pH 8.0 did not result in crystallization, as the protein precipitated or the drops remained clear. Direct measurement of crystallization tray pH with a pH microprobe showed that the well solution was approximately 1 pH unit more acidic than the drop solution. The closer the well and drop solutions were in pH (within 0.5 unit) the more often single crystals were obtained. Moving the crystals into buffered cryo solutions were initially unsuccessful, resulting in cracking of the crystals. Capillary mounting of a crystal allowed determination that the crystal was indeed protein and diffracted to about 3.3 Å in the X-ray facility. In order to increase the size of single crystals, streak seeding was used. NAD synthetase seeds were obtained from freshly grown (≦1-week) crystals. The Seed Bead kit (Hampton Research) was used to prepare a fresh seed stock. Using a washed cat whisker (a generous gift of MSHarris), seeds from prepared dilutions of the stock liquor were streaked into VDX trays containing 12–25% PEG 1500. Large crystals grew in 18–22% PEG 1500. Co-crystals were obtained by mixing the protein with the co-crystallization agent, either 5 mM AMP-PNP or 2 mM $N^{\alpha}AD$. Crystals of selenomethionine NAD synthetase were prepared in the same conditions as the native form. In order to utilize the beamlines available at the synchrotron, stable cryoprotectant solutions were necessary. After much experimentation (120 conditions), stable cryo conditions were found that both effectively buffered the crystal and protected it from freezing at 100K. This condition was 50 mM imidazole, pH 7.0, 20% PEG 1500, 12–17.5% glycerol. Transfer of the crystals had to be done with utmost caution, due to the fragility of the crystal. It was necessary to move them by capillary as opposed to cryoloops, because the transfer of crystal with stabilizing liquor was necessary to prevent cracking. Ten minute soaks in 0.05M imidazole, 20% PEG 1500 pH 7.0 with increasing amounts of glycerol from 5–20% (in 5% increments) were used to transfer the crystals into cryo conditions. Crystals were either left in the well after passing through the glycerol soaks, or looped out and flash frozen in liquid nitrogen.

B. X-Ray Diffraction Characterization

Data were collected at the synchrotron on a series of NAD synthetase crystals—selenomethionine and native NadE with and without the substrate, deamino NAD, and a substrate analog, AMP-PNP. Native NAD synthetase crystals in space group $P2_1$ with cell constants a=50.9 Å, b=107.7 Å, c=92.1 Å, α=γ=90°, β=97.7° diffracted to 2.2 Å at the synchrotron (Table 6).

TABLE 6

Data for native NadE crystal collected on the Mar CCD detector on beamline 17-ID with an exposure time of 4 sec and a frame width of 0.5°.

| | λ 1.0000 Å (12398.5 eV) |
|---|---|
| Resolution | 2.2 Å |
| No. observations | 180,573 |
| No. unique refl. | 49,216 |
| % completeness | 97.0% |
| $R_{sym}$ | 0.055 |

Because these data were of higher quality than the multiple anomalous dispersion data, a molecular replacement solution was initially attempted using the NadE dimer from *Bacillus subtilis* (1nsy.pdb (Rizzi et al., *EMBO J.*, 15:5125–34 (1996)). A rotation solution was found using AMORE (Navaza, *Acta Cryst.*, A50:157–63 (1994)) with a peak height of 8.6σ and a subsequent translation solution with a correlation coefficient of 26.9 and an R-factor of 50.3%. Subsequent refinement and rebuilding of this model (and other molecular replacement solutions from X-PLOR rotation/translation searches) led to an R-factor of 40% with a Free R-factor above 50%. Since this solution was difficult to refine, further efforts for a structure solution were attempted using the multiple anomalous dispersion data.

C. Heavy Atom Derivative

Although a multiple anomalous dispersion experiment (Hendrickson, *Science*, 254:51–58 (1991)) was conducted using selenomethionine NadE (Table 7), the crystals were very mosaic.

TABLE 7

Data collection and phasing statistics for a selenomethionine
NadE crystal collected on the Mar CCD detector on beamline
17-ID with a frame width of 1.0° (exposure times varied
from 1.5 sec to 3 sec).

|  | λ 1.0000 Å (12398.5 eV) | λ 0.979530 Å (12657.6 eV) | λ 0.97939 Å (12659.8 eV) |
|---|---|---|---|
| Resolution | 2.7 Å | 2.7 Å | 2.7 Å |
| No. observations | 193,570 | 160,332 | 181,537 |
| No. unique refl. | 26,919 | 25,427 | 26,471 |
| % completeness | 98.4% | 94.0% | 95.3% |
| $R_{sym}$ | 0.085 | 0.098 | 0.109 |
| $R_{cullis}$ acentrics | — | 0.88 | 0.88 |
| $R_{cullis}$ anomalous | — | 0.85 | 0.87 |
| Phasing power |  |  |  |
| centrics | — | 0.55 | 0.57 |
| acentrics | — | 0.77 | 0.76 |
| Mean figure of merit (to 2.7 Å resolution) |  | 0.436 |  |

Figure 1:
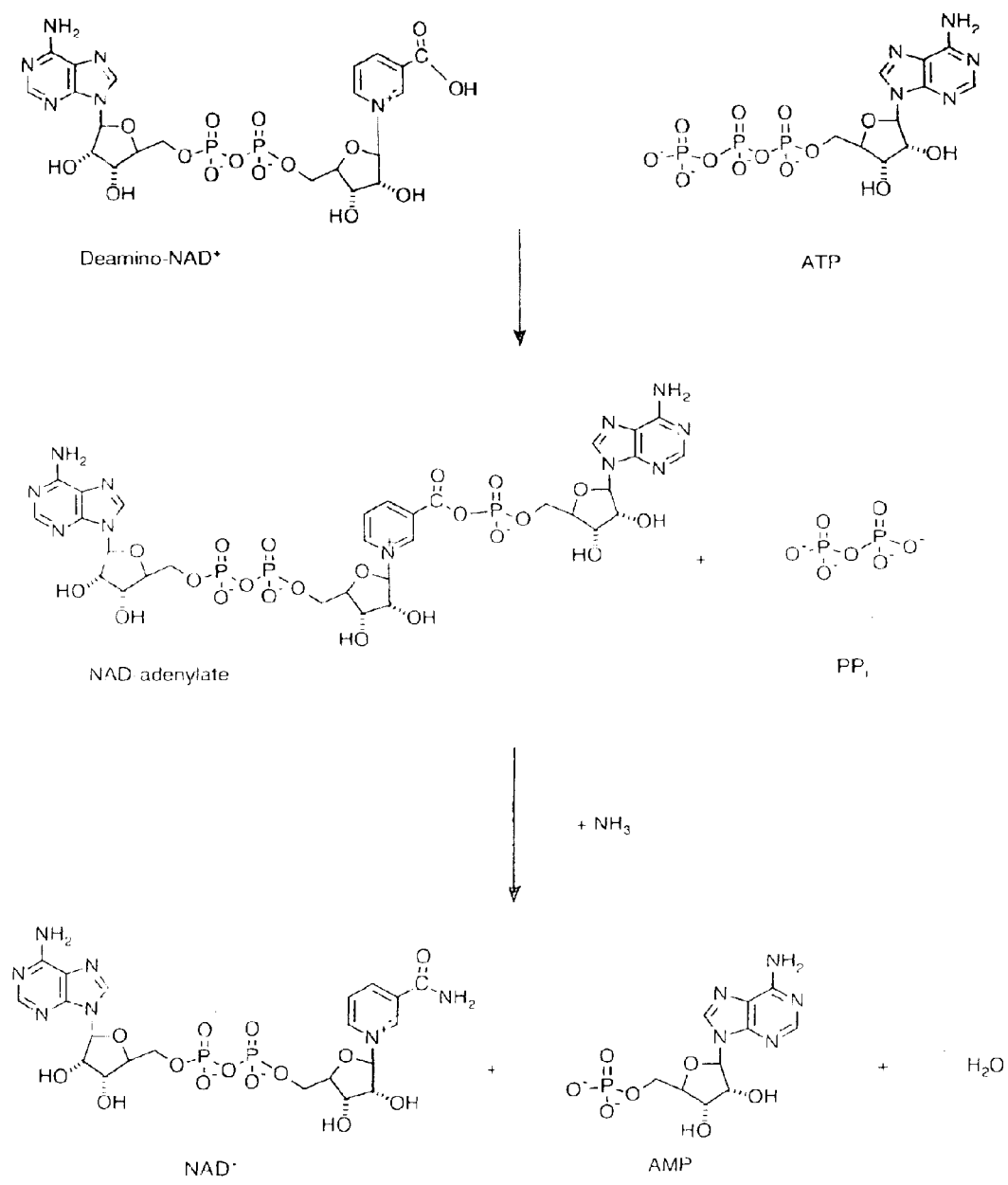
FIG. 1 depicts the reaction scheme for the synthesis of NAD$^+$ from deamino-NAD$^+$ and ATP catalyzed by NAD synthetase.
Figure 2A:
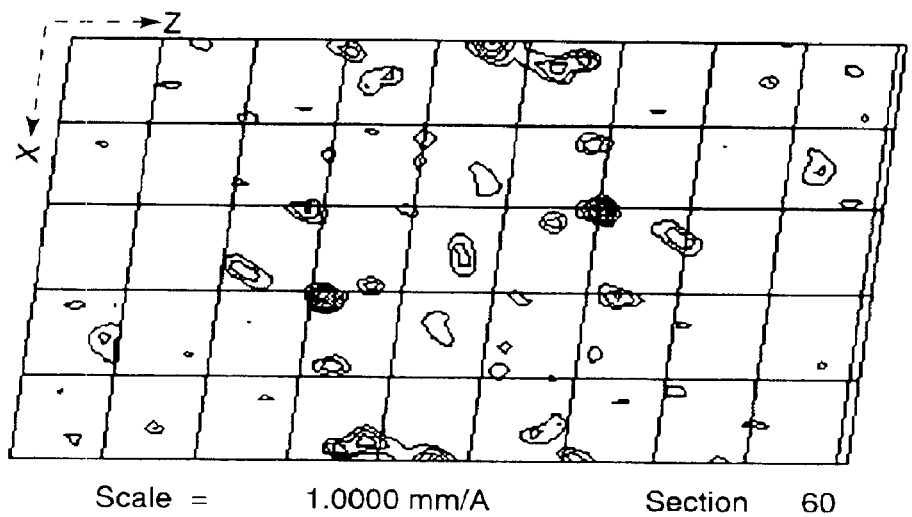
FIG. 2 illustrates a) a peak anomalous difference Patterson Map for Harker sections v=½ at 2.7 Å resolution and b) an edge anomalous difference Patterson Map for Harker sections v=½ at 2.7 Å resolution.
Figure 2B:
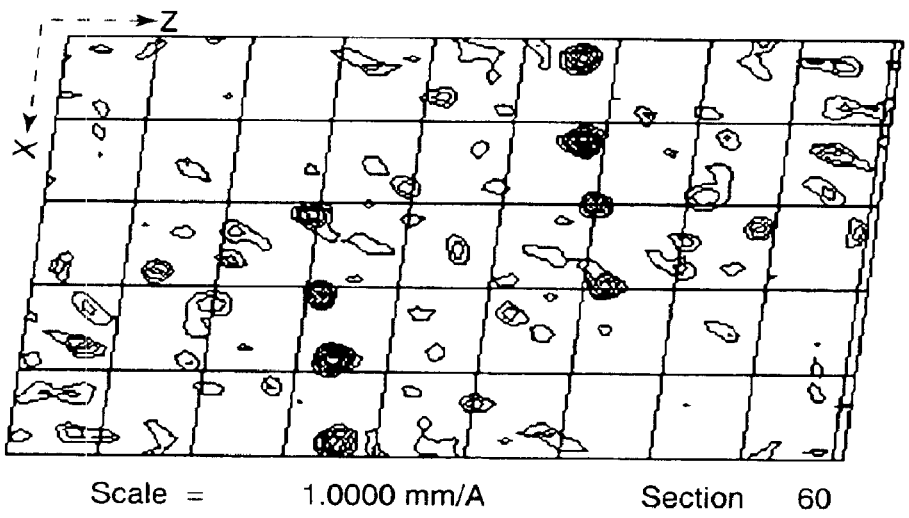
Figure 3A:
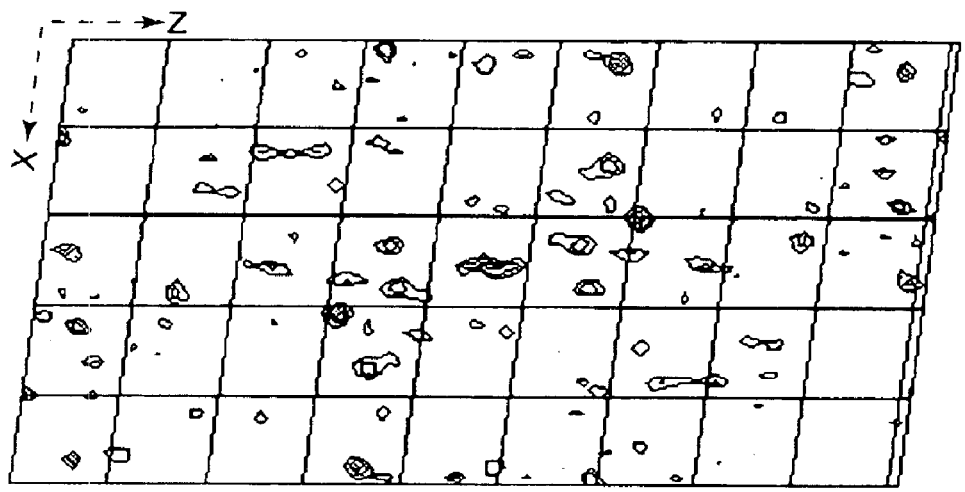
FIG. 3 illustrates a) an edge low dispersive difference Patterson Map for Harker sections v=½ at 2.7 Å resolution and b) a peak low dispersive difference Patterson Map for Harker sections v=½ at 2.7 Å resolution.
Figure 3B:
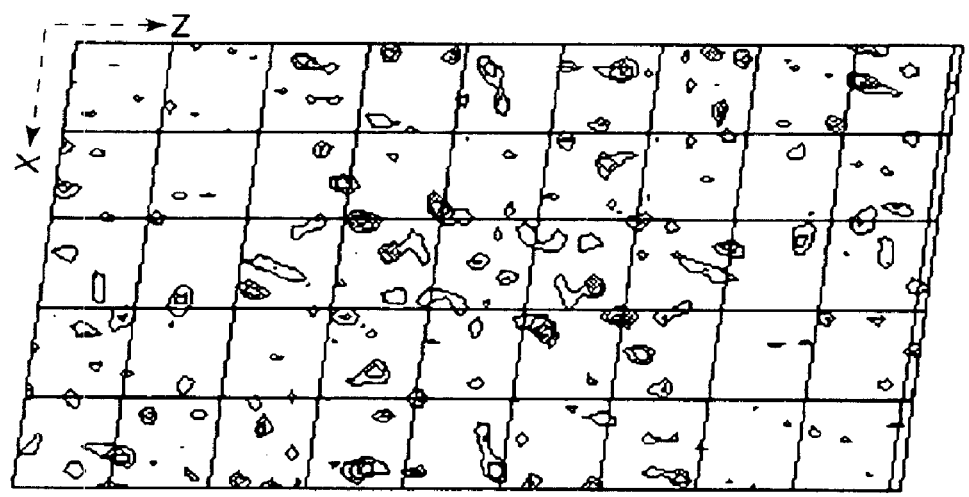

The resolution and quality of the anomalous and dispersive signals were poor making data interpretation difficult. A second data set collected on a selenomethionine incorporated NadE crystal grown in the presence of $N^{a}AD$ was also very mosaic suggesting a fundamental problem with the selenomethionine crystals and/or the cryogenic conditions used to preserve the crystals. However, the data was of sufficient quality at 2.7 Å to begin to identify heavy atom positions. Both anomalous and dispersive difference Patterson maps revealed the presence of at least four strong heavy atom peaks (FIGS. 2–3). A total of eight sites were identified using automated Patterson interpretation methods in SHELX (Sheldrick et al., *Acta Cryst.*, B51:423–31 (1995)). There are four methionines in each molecule of NadE excluding the N-terminal methionine. Therefore, the eight heavy atom positions would be consistent with the presence of two molecules in the asymmetric unit. Phasing with these eight sites led to electron density maps that were difficult to interpret suggesting that the positions of the heavy atom sites might be incorrect except for the fact that these sites were completely consistent with the Patterson maps. Methionine positions from the initial molecular replacement solutions described above using the NadE dimer from *Bacillus subtilis* were also consistent with the peaks in the Patterson maps making the difficulty in refinement and the low quality electron maps even more puzzling.

D. Molecular Replacement

Molecular replacement experiments were conducted with either AMORE (Navaza, *Acta Cryst.*, A50: 157–63 (1994)) or X-PLOR using the *B. subtilis* model of NAD synthetase (PDB id code 1nsy). A portion of the model (residues 106–125) was truncated where the identity of the two proteins was significantly lower than the remainder of the sequence. Using this truncated model, the initial solution for the first dimer gave a correlation coefficient of 18.8 with an R-factor of 51.2%. Searching for the second dimer led to an improved correlation coefficient of 30.0 with an R-factor of 48.5%.

Figure 4A:
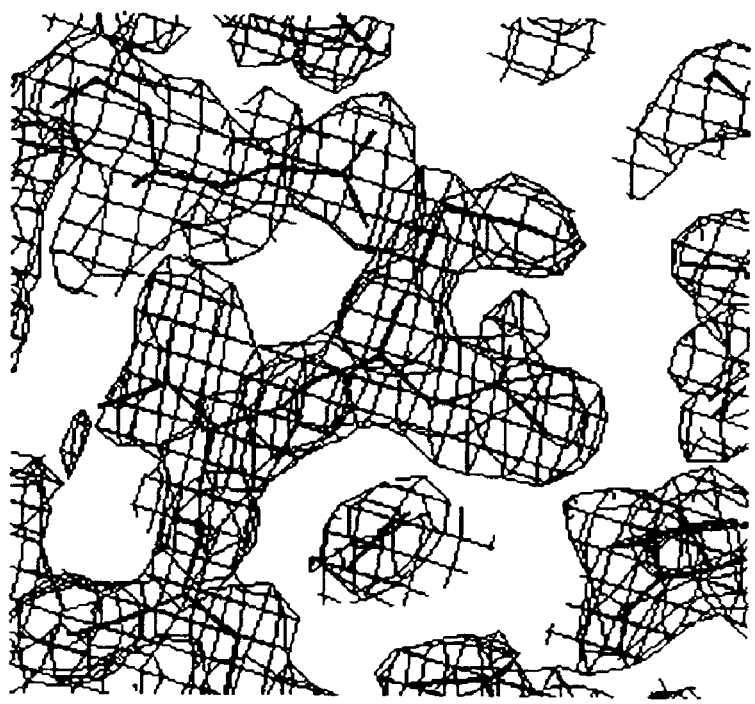
FIG. 4 depicts a) an electron density map of the molecular replacement solution after one cycle of simulated annealing, and b) the final 2Fo-Fc map.
Figure 4B:
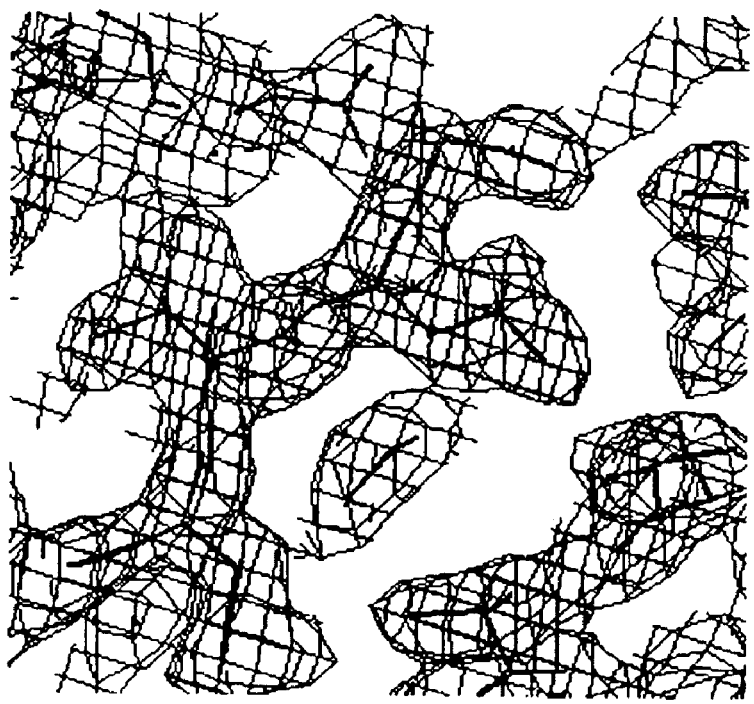

A closer look at the packing of the molecular replacement solution indicated that there was still a significant volume of the unit cell that remained unoccupied. This observation suggested that there indeed might be a second dimer present in the unit cell (for a total of four monomers in the asymmetric unit) potentially related by a translational symmetry operator (some of the selenium sites identified in the MAD experiment were related by translational symmetry which was consistent with this hypothesis). This possibility had been overlooked in part because the previous structure of NadE from *B. subtilis* had similar cell constants to the *S. aureus* NadE unit cell yet only one dimer in the asymmetric unit. But a careful calculation of the percent solvent content allowed for the *S. aureus* NadE unit cell indicated that for two molecules there would be 68.5% solvent and with four molecules there would be 37.0% solvent. For the *B. subtilis* unit cell, four molecules are unable to pack in the unit cell by solvent calculations. Working on this new hypothesis of the presence of four molecules in the asymmetric unit (two dimers), a translation search was conducted for the position of the second dimer by fixing the position of the first dimer using AMORE. A solution was found which gave good packing and an R-factor of 45.5% and a Free R-factor of 46.2% after rigid body refinement in X-PLOR (Brunger, X-PLOR version 3.1, Yale University Press (1992)) with a reasonably interpretable electron density map (FIG. 4). Subsequent refinement and rebuilding of the model has resulted in a model with R-factor of 25.0% and a Free R-factor of 34.7% (Table 8).

TABLE 8

Refinement Statistics for a native NadE data set.

|  | R-factor | Free R-factor | No. of reflections |
|---|---|---|---|
| 20–2.3 Å F ≧ 2σ | 0.226 | 0.312 | 42,369 |

|  | Bonds (Å) | Angles (°) |
|---|---|---|
| r.m.s deviation from ideal geometry | 0.010 | 1.76 |

|  | Number of atoms | Average B-factor |
|---|---|---|
| Protein | 8010 | 24.3 |
| Waters | 384 | 34.3 |
| Total | 8394 | 24.7 |

This is the first *S. aureus* protein structure with a reasonable rotation function signal using the model from another species (*B. subtilis* is a Gram positive organism like *S. aureus*).

Figure 5:
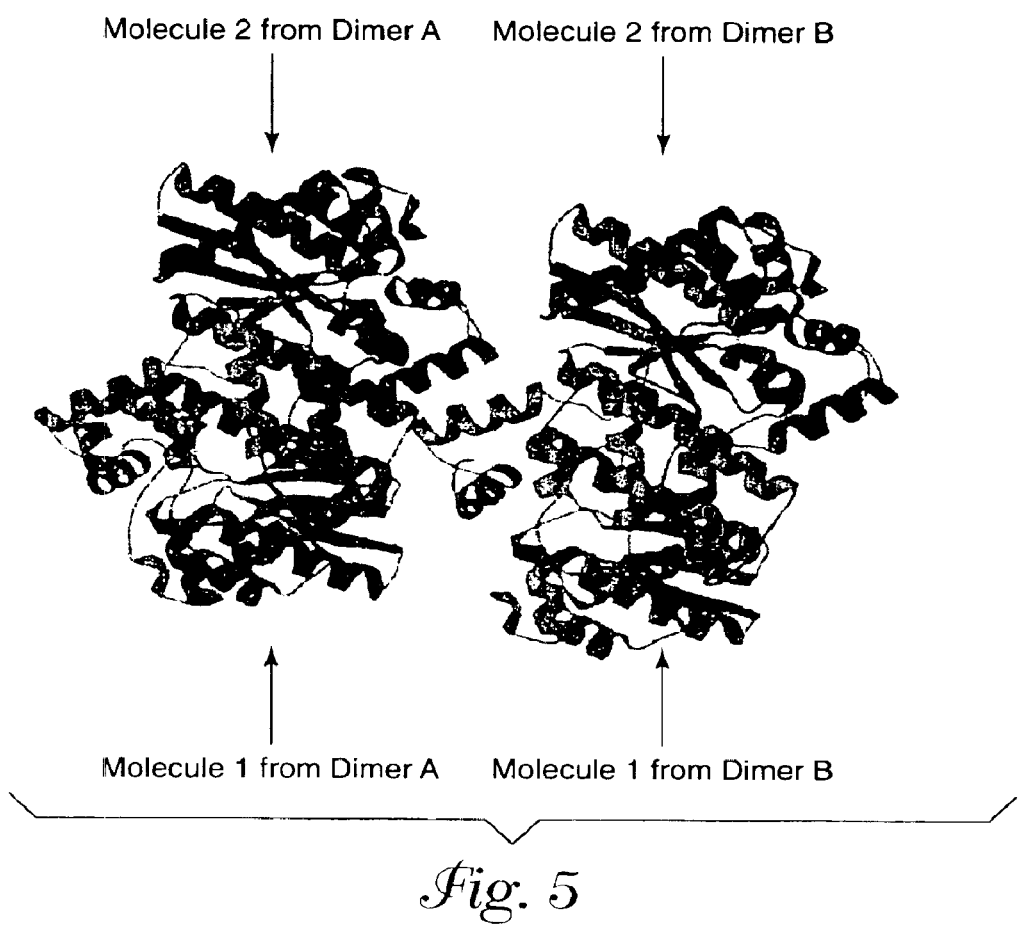
FIG. 5 illustrates the structure of the two *S. aureus* NAD synthetase dimers in the asymmetric unit related by translational symmetry.

The packing of the two dimers was reasonable and the two dimers in fact were related by a non-crystallographic translation symmetry element (FIG. 5). A short retrospective study was conducted using the multiple anomalous dispersion data to see if the MAD electron density was of higher quality than the molecular replacement solution. The 16 selenium atoms position were determined from the sulfur position of the methioinines from the molecular replacement solution within the asymmetric unit. Subsequent phasing using the 16 sites as determined by molecular replacement showed that the phase information derived from the MAD experiment was suboptimal (Table 7).

A third data set was collected on a native NadE crystal grown in the presence of AMP-PNP (Table 9).

TABLE 9

Data collection for a native NadE crystal grown
in the presence of AMP-PNP collected on the Mar CCD
detector on beamline 17-ID with an exposure time
of 2 sec and a frame width of 1.0°.

|  | λ 1.0000 Å (12398.5 eV) |
|---|---|
| Resolution | 2.2Å |
| No. observations | 187,042 |
| No. unique refl. | 49,121 |

TABLE 9-continued

Data collection for a native NadE crystal grown in the presence of AMP-PNP collected on the Mar CCD detector on beamline 17-ID with an exposure time of 2 sec and a frame width of 1.0°.

|  | λ 1.0000 Å (12398.5 eV) |
| --- | --- |
| % completeness | 99.2% |
| $R_{sym}$ | 0.050 |

Scaling of this data set to the native unbound data suggested that there were no significant differences between the two data sets. Analysis of the electron density did not reveal any ligand present in the active site, and, therefore, this data set was not analyzed further.

E. Phase Combination

The multiple anomalous dispersion (MAD) phasing were performed (2.7 Å resolution) using three different wavelengths (see Table 7). Each of individual data set was indexed and integrated separately (see Table 7 for integration statistics). The data sets for each experiment were scaled to each other using the program SCALEIT in the CCP4 Program Suite (Collaborative Computational Project N4, *Acta Cryst.*, D50:760–63 (1994)). Patterson maps revealed eight selenium sites whose locations were determined by direct methods using SHELX (Sheldrick et al., *Acta Cryst.*, B51:423–31 (1995)). All heavy atom parameter refinement and phasing calculations were carried out with MLPHARE (Otwinowski, Isomorphous Replacement and Anomalous Scattering, W. Wolf, P. R. Evans, and A. G. W. Leslie, eds, 80–86 (1991) and Collaborative Computational Project N4,*Acta Cryst.,* D50:760–63 (1994)) by treating the remote wavelength as native and the edge and peak wavelengths as derivatives (Ramakrishnan et al., *Nature,* 362:219–23 (1993)). The phases were subsequently subjected to solvent flattening using the program DM (Cowtan, *Acta Cryst.,* D49:148–57 (1993), Cowtan, *Acta Cryst.,* D54:487–93 (1998), and Collaborative Computational Project N4, *Acta Cryst.,* D50:760–63 (1994)).

F. Model Building and Refinement

Model building was done using the program CHAIN (Sack *J. Molecular Graphics,* 6:224–25 (1988)) and LORE (Finzel, *Meth. Enzymol.,* 277:230–42 (1997)). Model for one dimer built using the *B. subtilis* NAD synthetase structure as a reference. The second dimer was placed using non-crystallographic translational symmetry from the molecular replacement solution (R-factor/Free R-factor=34.1%/39.9%), and refined using positional refinement, torsion angle dynamics and individual B-factor refinement (R-factor/Free R-factor=24.9%/34.7%). At this stage waters were added and each monomer was thoroughly checked against the electron density. A further rounds of refinement led to the present model (R-factor/Free R-factor=22.6%/31.2%). All refinement cycles were carried out with XPLOR98 (Brunger, X-PLOR version 3.1, Yale University Press (1992)) incorporating bulk solvent correction during the refinement (Jiang et al., *J. Mol. Biol.,* 243:100–15 (1994)). Progress of the refinement was monitored by a decrease in both the R-factor and Free R-factor. Stereochemistry of the model was checked using PROCHECK (Laskowski et al, *J. Appl. Cryst.,* 26:283–91 (1993)) revealing no residues in disallowed regions of the Ramachandran plot. FIG. 5 was produced in MOLSCRIPT (Kraulis, *J. Appl. Cryst.,* 24:946–50 (1991)) and Raster 3D (Merritt et al.,*Acta Cyst.,* D50:869–73 (1994) while FIGS. 6–8 were produced in MOLSCRIPT (Kraulis, *J. Appl. Cryst.,* 24:946–50 (1991)) alone. FIGS. 11 and 12 were created in Mosaic-2.

The complete disclosure of all patents, patent applications including provisional applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described; many variations will be apparent to one skilled in the art and are intended to be included within the invention defined by the claims.

SEQUENCE LISTING FREE TEXT

SEQ ID NO:1 recombinant *S. aureus* nicotinamide adenine dinucleotide (NAD)
SEQ ID NO: 2 recombinant *B. subtilis* nicotinamide adenine dinucleotide (NAD)

What is claimed is:

1. A crystal of *Staphylococcus aureus* nicotinamide adenine dinucleotide (*S. aureus* NAD) synthetase having the monoclinic space group symmetry P2$_1$.

2. A crystal of *Staphylococcus aureus* nicotinamide adenine dinucleotide (*S. aureus* NAD) synthetase comprising a unit cell having dimensions of a, b, and c; wherein a is about 40 Å to about 60 Å, b is about 90 Å to about 120 Å, and c is about 80 Å to about 110 Å; and wherein α=γ=90° and β is about 80° to about 120°.

3. A crystal of *Staphylococcus aureus* nicotinamide adenine dinucleotide (*S. aureus* NAD) synthetase comprising atoms arranged in a spatial relationship represented by the structure coordinates listed in Table 1.

4. A crystal of *Staphylococcus aureus* nicotinamide adenine dinucleotide (*S. aureus* NAD) synthetase having amino acid sequence SEQ ID NO:1.

5. A crystal of *Staphylococcus aureus* nicotinamide adenine dinucleotide (*S. aureus* NAD) synthetase having amino acid sequence SEQ ID NO:1, with the proviso that at least one methionine is replaced with selenomethionine.

6. A method for crystallizing *Staphylococcus aureus* nicotinamide adenine dinucleotide (*S. aureus* NAD) synthetase comprising:
   providing purified *S. aureus* NAD synthetase at a concentration of about 1 mg/ml to about 50 mg/ml; and
   forming a crystal of *S. aureus* NAD synthetase from a solution comprising 18% by weight to 22% by weight polyethylene glycol (PEG) 1500 and about 0% by weight to about 20% by weight dimethyl sulfoxide (DMSO),
   wherein the crystal has the monoclinic space group symmetry P2$_1$.

7. A method for crystallizing *Staphylococcus aureus* nicotinamide adenine dinucleotide (*S. aureus* NAD) synthetase comprising:
   providing purified *S. aureus* NAD synthetase at a concentration of about 1 mg/ml to about 50 mg/ml; and
   forming a crystal of *S. aureus* NAD synthetase from a solution comprising 18% by weight to 22% by weight polyethylene glycol (PEG) 1,500 and about 0% by weight to about 20% by weight dimethyl sulfoxide (DMSO),
   wherein the crystal comprises a unit cell having dimensions of a, b, and c; wherein a is about 40 Å to about 60 Å, b is about 90 Å to about 120 Å, and c is about 80 Å to about 110 Å; and wherein α=γ=90° and β is about 80° to about 120°.

8. A method for crystallizing *Staphylococcus aureus* nicotinamide adenine dinucleotide (*S. aureus* NAD) synthetase comprising:
   providing purified *S. aureus* NAD synthetase at a concentration of about 1 mg/ml to about 50 mg/ml; and
   forming a crystal of *S. aureus* NAD synthetase from a solution comprising 18% by weight to 22% by weight polyethylene glycol (PEG) 1,500 and about 0% by weight to about 20% by weight dimethyl sulfoxide (DMSO),
   wherein the crystal comprises atoms arranged in a spatial relationship represented by the structure coordinates listed in Table 1.

9. A method for crystallizing *Staphylococcus aureus* nicotinamide adenine dinucleotide (*S. aureus* NAD) synthetase comprising:
   providing purified *S. aureus* NAD synthetase at a concentration of about 1 mg/ml to about 50 mg/ml; and
   forming a crystal of *S. aureus* NAD synthetase from a solution comprising 18% by weight to 22% by weight polyethylene glycol (PEG) 1500 and about 0% by weight to about 20% by weight dimethyl sulfoxide (DMSO),
   wherein the crystal of *S. aureus* NAD synthetase has an *S. aureus* NAD synthetase amino acid sequence SEQ ID NO:1.

10. A method for crystallizing *Staphylococcus aureus* nicotinamide adenine dinucleotide (*S. aureus* NAD) synthetase comprising:
    providing purified *S. aureus* NAD synthetase at a concentration of about 1 mg/ml to about 50 mg/ml; and
    forming a crystal of *S. aureus* NAD) synthetase from a solution comprising 18% by weight to 22% by weight polyethylene glycol (PEG) 1,500 and about 0% by weight to 20% by weight dimethyl sulfoxide (DMSO),
    wherein the crystal of *S. aureus* NAD synthetase has an *S. aureus* NAD synthetase amino acid sequence SEQ ID NO:1, except that at least one methionine is replaced with selenomethionine.

11. A crystal of *Staphylococcus aureus* nicotinamide adenine dinucleotide (*S. aureus* NAD) synthetase, wherein the crystal diffracts x-rays to a resolution of 1.5 Å to 3 Å.

12. The crystal of claim 11 wherein the resolution is at least 2.2 Å.

13. A crystal of *Staphylococcus aureus* nicotinamide adenine dinucleotide (*S. aureus* NAD) synthetase, wherein the crystal has at least one dimension of 0.15–0.8 mm.

14. The crystal of claim 13 having dimensions of 0.15–0.8 mm×0.2 mm×0.05–0.1 mm.

15. The crystal of claim 13 wherein the crystal diffracts x-rays to a resolution of 1.5 Å to 3 Å.

16. The crystal of claim 15 wherein the resolution is at least 2.2 Å.

* * * * *